(12) United States Patent
Park et al.

(10) Patent No.: US 12,234,207 B2
(45) Date of Patent: Feb. 25, 2025

(54) HALO-(3-(PHENYLSULFONYL)PROP-1-ENYL)PYRIDINE DERIVATIVE AND USE THEREOF

(71) Applicant: Cureverse Incorporated, Seoul (KR)

(72) Inventors: Ki Duk Park, Seoul (KR); Ae Nim Pae, Seoul (KR); Sang Min Lim, Seoul (KR); Jong Hyun Park, Seoul (KR); Ji Won Choi, Seoul (KR); Siwon Kim, Seoul (KR); Hyeon Jeong Kim, Seoul (KR); Seul Ki Yeon, Seoul (KR)

(73) Assignee: CUREVERSE INCORPORATED, Seoul (KR)

( * ) Notice: Subject to any disclaimer, the term of this patent is extended or adjusted under 35 U.S.C. 154(b) by 1046 days.

(21) Appl. No.: 17/268,958

(22) PCT Filed: Aug. 19, 2019

(86) PCT No.: PCT/KR2019/010513
§ 371 (c)(1),
(2) Date: Mar. 16, 2021

(87) PCT Pub. No.: WO2020/036474
PCT Pub. Date: Feb. 20, 2020

(65) Prior Publication Data
US 2021/0317083 A1 Oct. 14, 2021

(30) Foreign Application Priority Data

Aug. 17, 2018 (KR) .................. 10-2018-0096167

(51) Int. Cl.
*C07D 213/52* (2006.01)
*C07F 9/40* (2006.01)

(52) U.S. Cl.
CPC .......... *C07D 213/52* (2013.01); *C07F 9/4071* (2013.01)

(58) Field of Classification Search
CPC .. C07D 213/52; C07D 213/61; C07D 239/30; C07D 401/12; C07D 413/12; C07F 9/4071; A61P 11/00; A61P 13/12; A61P 17/06; A61P 25/00; A61P 25/08; A61P 25/16; A61P 25/22; A61P 25/24; A61P 25/28; A61P 1/16; A61K 31/44; A61K 31/496; A61K 31/5355
See application file for complete search history.

(56) References Cited

U.S. PATENT DOCUMENTS

| 5,510,490 A | 4/1996 | Pandey et al. |
| 2002/0022666 A1 | 2/2002 | Reddy et al. |
| 2017/0226073 A1 | 8/2017 | Copland, III et al. |

FOREIGN PATENT DOCUMENTS

| KR | 1020030036993 A | 5/2003 |
| KR | 1020130122420 A | 11/2013 |
| WO | 2017136589 A1 | 8/2017 |

OTHER PUBLICATIONS

Ratushnyy, M., "A mild light-induced cleavage of the S—O bond of aryl sulfonate esters enables efficient sulfonylation of vinylarenes." Chemical Science 9.36 (2018): 7193-7197.*
Seo Yeon Woo et al., "Discovery of Vinyl Sulfones as a Novel Class of Neuroprotective Agents toward Parkinson's Disease Therapy," Journal of Medicinal Chemistry, 2014, pp. 1473-1487, vol. 57, American Chemical Society.
Ji Won Choi et al., "Optimization of Vinyl Sulfone Derivatives as Potent Nuclear Factor Erythroid 2-Related Factor 2 (Nrf2) Activators for Parkinson's Disease Therapy," Journal of Medicinal Chemistry, Dec. 12, 2018, pp. 811-830, vol. 62.
International Search Report mailed Dec. 2, 2019 for PCT/KR2019/010513.
Indian Office Action for IN Application No. 202117011414 mailed on Nov. 1, 2023.

* cited by examiner

*Primary Examiner* — John M Mauro
(74) *Attorney, Agent, or Firm* — CANTOR COLBURN LLP

(57) ABSTRACT

The present invention relates to a novel halo-(3-(phenylsulfonyl)prop-1-enyl)pyridine derivative or a pharmaceutically acceptable salt thereof; a preparation method thereof; and an Nrf2 activator and a pharmaceutical composition for preventing or treating diseases induced by a decrease in Nrf2 activity, both of which comprise the same as an active ingredient.

20 Claims, 4 Drawing Sheets

HALO-(3-(PHENYLSULFONYL)PROP-1-ENYL)PYRIDINE DERIVATIVE AND USE THEREOF

TECHNICAL FIELD

The present invention relates to a novel halo-(3-(phenylsulfonyl)prop-1-enyl)pyridine derivative or a pharmaceutically acceptable salt thereof; a preparation method thereof; and an Nrf2 activator and a pharmaceutical composition for preventing or treating diseases induced by a decrease in Nrf2 activity, both of which comprise the same as an active ingredient.

BACKGROUND ART

Nuclear factor erythroid-derived 2-related factor 2 (Nrf2) is a transcription factor of the cap 'n' collar (CNC) family of basic region leucine zipper (bZIP) and induces transcription of genes by binding to the antioxidant response element (ARE) sequence, which is a region involved in expression of various genes that protect cells. Although the expression of all antioxidant enzymes is not induced by ARE inducers, the finding that the expression of antioxidant enzymes is induced by ARE-mediated Nrf2 activation has been revealed through studies using Nrf2-null mice in which the transcription factor was artificially knocked out.

Nrf2 is negatively controlled by Kelch-like ECH-associated protein 1 (Keap1). In this regard, under no oxidative stress conditions, Nrf2 binds to Keap1, which becomes ubiquitinated and is decomposed by proteasome, but under oxidative stress conditions, the binding of Nrf2 is removed through the modification of the cysteine residue of Keap1, and Nrf2 moves into the nucleus and binds to ARE, increasing the transcription of various antioxidant genes in the promoter region.

In natural products, foods, metabolites, organic synthetic compounds, etc., compounds of various structures that cause transcription of protective genes through the Nrf2-Keap1 pathway have been discovered. All of the compounds known so far are electrophilic compounds that can react with cysteine of Keap1 or are compounds that change into electrophilic compounds through intracellular metabolic processes. Such electrophilic compounds or reactive oxygen species react with the cysteine residue of Keap1 to oxidize the thiol group, or form a covalent bond to cause a structural change of Keap1. Nrf2 isolated due to the change in the cysteine residue of Keap1 moves to the nucleus and binds to ARE, thereby inducing the expression of antioxidant enzymes. It has been reported that Nrf2 activators can prevent the development of degenerative brain diseases as a chemical defense mechanism against oxidative stress by pre-activating the Nrf2-Keap1 pathway using electrophilic compounds.

As a drug that can react with the cysteine residue of Keap1, sulforaphane (1-isothiocyanato-4-methylsulfinylbutane) is mainly present in cruciferous plants such as broccoli, Chinese cabbage, etc., and protects dopaminergic neurons from oxidative stress by activating Nrf2. However, sulforaphane can induce cytotoxicity by non-selectively denaturing various proteins in cells having thiol groups, and has a disadvantage of having very low blood-brain barrier permeability. Additionally, since it is dissipated within 1 hour when administered into the body, the effect of inducing Nrf2 activity cannot be sustained, and accordingly, when administered at a high concentration to show a certain activity, it causes cytotoxicity.

Therefore, there is a need to develop a novel Nrf2 activator that can overcome the problems of the existing Nrf2 activators. In this context, VSC2, which is a compound having excellent activity among a series of chalcone derivatives known to induce activation of Nrf2 through structural changes of Keap1, has been discovered (Woo et al. Journal of Medicinal Chemistry 2014, 57, 1473-1487). However, VSC2 has low bioavailability and drug metabolic stability when administered into the body, has low solubility in water, and has cardiac toxicity caused by drugs, and thus, there is still a need to find a drug that can overcome such problems.

DISCLOSURE

Technical Problem

The present inventors have made extensive efforts to discover a novel small-molecule compound that activates Nrf2, which is involved in a defense mechanism against oxidative stress, for the prevention or treatment of various diseases caused by oxidative stress, and as a result, they have confirmed that derivatives, in which halopyridinyl groups are substituted in the vinyl group of a (vinylsulfonyl) benzene structure, and halogen, alkylpiperazinyl, or morpholinyl groups are substituted in the benzene ring, effectively activate Nrf2 and do not show toxicity at the active concentration, thereby completing the present invention.

Technical Solution

It is a first object of the present invention to provide a compound represented by Chemical Formula 1 below or a pharmaceutically acceptable salt thereof:

[Chemical Formula 1]

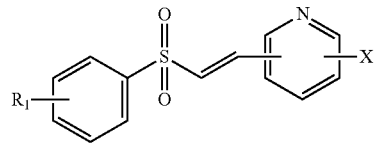

In the Chemical Formula 1,
$R_1$ is a halogen,

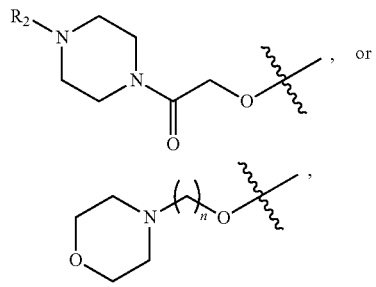

$R_2$ is hydrogen or $C_{1-4}$ alkyl,
n is an integer of 1 to 5, and
X is a halogen.

It is a second object of the present invention to provide a method for producing the compound of the first object or a pharmaceutically acceptable salt thereof, including reacting diethyl (($R_1$-substituted phenyl)sulfonyl)methylphosphonate with halopicolinealdehyde.

It is a third object of the present invention to provide a nuclear factor erythroid-derived 2-related factor 2 (Nrf2) activator including the compound of the first object or a pharmaceutically acceptable salt thereof as an active ingredient.

It is a fourth object of the present invention to provide a pharmaceutical composition for preventing or treating diseases induced by a decrease in Nrf2 activity, including the compound of the first object or a pharmaceutically acceptable salt thereof as an active ingredient.

It is a fifth object of the present invention to provide a method for preventing or treating diseases induced by a decrease in Nrf2 activity in an individual, including administering the pharmaceutical composition of the fourth object to an individual in need.

Advantageous Effects

The novel halo-(3-(phenylsulfonyl)prop-1-enyl)pyridine derivative of the present invention can activate Nrf2, and thus, it can be effectively used in the treatment or prevention of diseases induced by a decrease in Nrf2 activity.

DETAILED DESCRIPTION OF PREFERRED EMBODIMENTS

Figure 1:
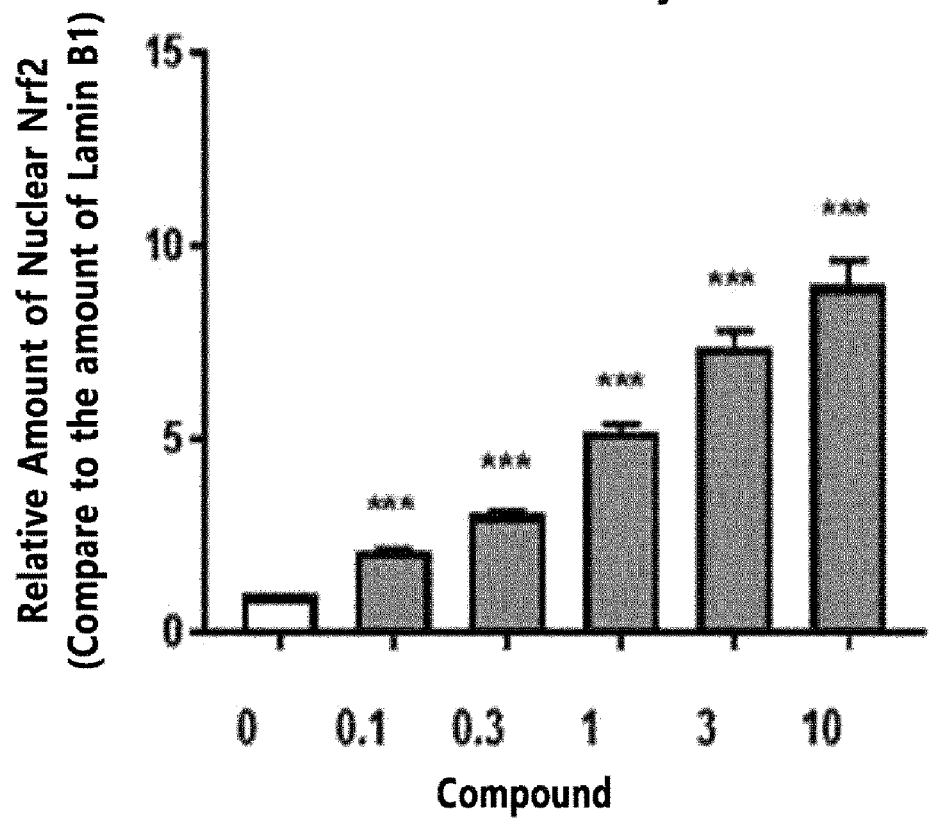
FIG. 1 is a diagram showing the result of quantitatively analyzing the activation of Nrf2 in the nucleus according to the concentration of the compound according to one embodiment of the present invention.

The first aspect of the present invention provides a compound represented by Chemical Formula 1 below or a pharmaceutically acceptable salt thereof:

[Chemical Formula 1]

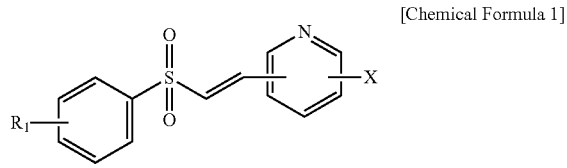

In the Chemical Formula 1
$R_1$ is a halogen, O, or

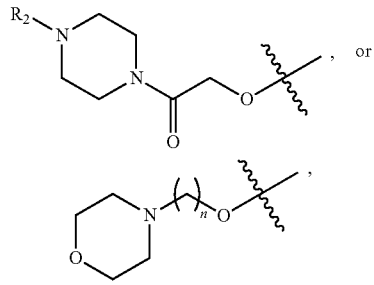

$R_2$ is hydrogen or $C_{1-4}$ alkyl,
n is an integer of 1 to 5, and
X is a halogen.

For example, the compound of the present invention may be a compound, wherein $R_1$ is chlorine or fluorine, and X is chlorine or fluorine.

Additionally, the compound of the present invention may be a compound, wherein $R_1$ is

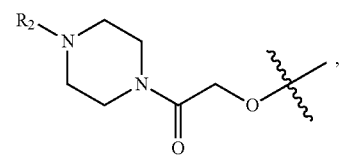

$R_2$ is methyl, and X is chlorine or fluorine, but the compound is not limited thereto.

Further, the compound of the present invention may be a compound, wherein $R_1$ is

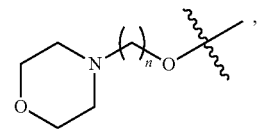

n is 3, and X is chlorine or fluorine, but the compound is not limited thereto.

Specifically, the compound may be
1. (E)-3-fluoro-2-(2-(2-fluorophenylsulfonyl)vinyl)pyridine,
2. (E)-3-fluoro-2-(2-(3-fluorophenylsulfonyl)vinyl)pyridine,
3. (E)-3-fluoro-2-(2-(4-fluorophenylsulfonyl)vinyl)pyridine,
4. (E)-3-chloro-2-(2-(2-fluorophenylsulfonyl)vinyl)pyridine,
5. (E)-3-chloro-2-(2-(3-fluorophenylsulfonyl)vinyl)pyridine,
6. (E)-3-chloro-2-(2-(4-fluorophenylsulfonyl)vinyl)pyridine,
7 (E)-2-(2-(2-chlorophenylsulfonyl)vinyl)-3-fluoropyridine,
8. (E)-2-(2-(3-chlorophenylsulfonyl)vinyl)-3-fluoropyridine,
9. (E)-2-(2-(4-chlorophenylsulfonyl)vinyl)-3-fluoropyridine,
10. (E)-3-chloro-2-(2-(2-chlorophenylsulfonyl)vinyl)pyridine, 11. (E)-3-chloro-2-(2-(3-chlorophenylsulfonyl)vinyl) pyridine,
12. (E)-3-chloro-2-(2-(4-chlorophenylsulfonyl)vinyl) pyridine,
13. (E)-2-chloro-6-(2-(2-chlorophenylsulfonyl)vinyl)pyrimidine,
14. (E)-2-chloro-3-(2-(2-chlorophenylsulfonyl)vinyl)pyrimidine,
15. (E)-4-(3-(4-(2-(3-fluoropyridin-2-yl)vinylsulfonyl) phenoxy)propyl)morpholine,
16. (E)-4-(3-(3-(2-(3-fluoropyridin-2-yl)vinylsulfonyl) phenoxy)propyl)morpholine,
17. (E)-2-(4-(2-(3-fluoropyridin-2-yl)vinylsulfonyl)phenoxy)-1-(4-methylpiperazin-1-yl)ethenone, or
18. (E)-2-(4-(2-(3-chloropyridin-2-yl)vinylsulfonyl)phenoxy)-1-(4-methylpiperazin-1-yl)ethenone.

The compound of the present invention may exist in the form of a pharmaceutically acceptable salt. An acid addition salt formed by a pharmaceutically acceptable free acid may be useful as the salt. As used herein, the term "pharmaceutically acceptable salt" refers to any organic or inorganic acid addition salt of the compound, which has a concentration such that it exhibits an effective action that is relatively non-toxic and harmless to patients and whose side effects caused by the salt do not impair the beneficial effect of the compound represented by Chemical Formula 1.

The acid addition salt may be prepared by a conventional method, for example, by dissolving the compound in an excess amount of acid aqueous solution, and then precipitating the salt using a water-miscible organic solvent such as methanol, ethanol, acetone, or acetonitrile. An acid or alcohol (e.g., glycol monomethyl ether) may be heated in an equal molar amount of the compound and water, and then the mixture may be dried by evaporation, or the precipitated salt may be suction-filtered.

Herein, as the free acid, an organic acid and an inorganic acid may be used. As the inorganic acid, hydrochloric acid, phosphoric acid, sulfuric acid, nitric acid, tartaric acid, etc. may be used, and as the organic acid, methanesulfonic acid, p-toluenesulfonic acid, acetic acid, trifluoroacetic acid, maleic acid, succinic acid, oxalic acid, benzoic acid, tartaric acid, fumaric acid, mandelic acid, propionic acid, citric acid, lactic acid, glycolic acid, gluconic acid, galacturonic acid, glutamic acid, glutaric acid, glucuronic acid, aspartic acid, ascorbic acid, carbonic acid, vanillic acid, hydroiodic acid, etc. may be used, but the acid is not limited thereto.

Further, a pharmaceutically acceptable metal salt may be prepared using a base. An alkali metal salt or an alkaline earth metal salt is, for example, obtained by dissolving a compound in an excess amount of an alkali metal hydroxide or an alkaline earth metal hydroxide solution, filtering undissolved compound salts, and then evaporating and drying the filtrate. Herein, it is preferable that a sodium, potassium, or calcium salt be prepared as the metal salt in a pharmaceutical aspect, but the salt is not limited thereto. Also, a silver salt corresponding to the metal salt may be obtained by allowing an alkali metal salt or an alkaline earth metal salt to react with a suitable silver salt (e.g., silver nitrate).

The pharmaceutically acceptable salt of the compound of the present invention may include a salt of an acidic or basic group, which can be present in the compound of Chemical Formula 1, unless otherwise specifically indicated. For example, the pharmaceutically acceptable salt may include a sodium salt, a calcium salt, and a potassium salt of a hydroxy group, and other pharmaceutically acceptable salts of an amino group may include hydrobromide, sulfate, hydrogen sulfate, phosphate, hydrogen phosphate, dihydrogen phosphate, acetate, succinate, citrate, tartrate, lactate, mandelate, methanesulfonate (mesylate), p-toluenesulfonate (tosylate), etc. Further, these salts may be prepared by a preparation method known in the art.

The pharmaceutically acceptable salt of the compound represented by Chemical Formula 1 of the present invention is a pharmaceutically acceptable salt, and any salt of the compound represented by Chemical Formula 1, which exhibits the same pharmacological activity as the compound of Formula 1, for example, which induces the activation of nuclear factor erythroid-derived 2-related factor 2 (Nrf2), can be used without limitation.

The second aspect of the present invention provides a method for producing the compound of the first aspect or a pharmaceutically acceptable salt thereof, including reacting diethyl (($R_1$-substituted phenyl)sulfonyl)methylphosphonate with halopicolinealdehyde.

Herein, the $R_1$ may be halogen

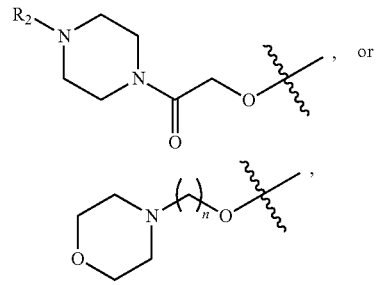

as defined in the first aspect.

For example, the preparation method of the present invention may be carried out by cooling a mixture of diethyl (($R_1$-substituted phenyl)sulfonyl)methylphosphonate and halopicolinealdehyde to −100° C. to −60° C. under anhydrous organic solvent conditions, and then adding butyllithium, but is not limited thereto, and may be carried out by a method known in the art without limitation.

The preparation method of the present invention may further include allowing to react with an excess acidic solution after the reaction, in order to provide the compound represented by Chemical Formula 1 in the form of a salt, but is not limited thereto.

For example, in the preparation method of the present invention, when $R_1$ is

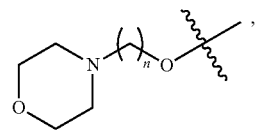

diethyl (($R_1$-substituted phenyl)sulfonyl)methylphosphonate used as a reactant may be prepared through:

Step a-1 of reacting (hydroxy-$C_{1-5}$ alkyl)morpholine with methanesulfonyl halide to prepare morpholino($C_{1-5}$ alkyl) methanesulfonate; and Step a-2 of reacting morpholino($C_{1-5}$ alkyl) methanesulfonate with diethyl (hydroxyphenylsulfonyl)methylphosphonate, but is not limited thereto. For example, commercially available products may be purchased and used, or those synthesized by using and/or modifying methods known in the art may be used without limitation.

Herein, the Step a-1 may be carried out by adding methanesulfonyl halide and a base to a solution in which (hydroxy-$C_{1-5}$ alkyl)morpholine is dissolved in an organic solvent at −10° C. to 10° C., and then reacting at 10° C. to 35° C., but is not limited thereto, and may be carried out by using and/or modifying reactions known in the art without limitation.

For example, a tertiary amine such as triethylamine, etc. may be used as the base. However, the scope of the present invention is not limited thereto, and as long as it can provide a basic reaction environment, basic reagents known in the art, such as NaOH, may be used without limitation.

Meanwhile, the Step a-2 may be carried out by mixing the reactants at 10° C. to 35° C. and heating to 70° C. to 90° C. in the presence of 1 to 2 equivalents of $K_2CO_3$ based on the amount of diethyl (hydroxyphenylsulfonyl)methylphosphonate used, but is not limited thereto, and may be carried out by using and/or modifying reactions known in the art without limitation.

For example, in the preparation method of the present invention, when $R_1$ is

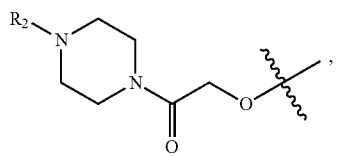

diethyl (($R_1$-substituted phenyl)sulfonyl)methylphosphonate used as a reactant may be prepared through:

Step b-1 of reacting diethyl (hydroxyphenylsulfonyl)methylphosphonate with $C_{1-4}$ alkyl haloacetate to prepare $C_{1-4}$ alkyl (((diethoxyphosphoryl)methylsulfonyl)phenoxy)acetate;

Step b-2 of converting ethyl (((diethoxyphosphoryl)methylsulfonyl)phenoxy)acetate to (((diethoxyphosphoryl)methylsulfonyl)phenoxy)acetic acid by sequentially treating with a basic solution and an acidic solution; and Step b-3 of reacting (((diethoxyphosphoryl)methylsulfonyl)phenoxy)acetic acid with piperazine or 1-($C_{1-4}$ alkyl) piperazine in the presence of 2 to 4 equivalents of carbonyldiimidazole to prepare diethyl ((2-(4-piperazin-1-yl)-2-oxoethoxy)phenylsulfonyl)methylphosphonate or diethyl ((2-(4-($C_{1-4}$ alkyl)piperazin-1-yl)-2-oxoethoxy)phenylsulfonyl)methylphosphonate, but is not limited thereto. For example, commercially available products may be purchased and used, or those synthesized by using and/or modifying methods known in the art may be used without limitation.

Specifically, in the preparation method of the present invention, the Step b-1 may be carried out by heating the mixture to 80° C. to 10000 in the presence of 1 to 2 equivalents of $K_2CO_3$ based on the amount of diethyl (hydroxyphenylsulfonyl)methylphosphonate used, but is not limited thereto, and may be carried out by using methods known in the art without limitation.

For example, the Step b-2 may be carried out at 10° C. to 40°, but is not limited thereto, and it is obvious to those skilled in the art that the reaction may be carried out by controlling the reaction temperature in an appropriate range in order to increase the efficiency and/or yield of the reaction.

Further, the Step b-3 may be carried out by reacting the reactant with carbonyldiimidazole at 10° C. to 40° C., and then adding piperazine or 1-($C_{1-4}$ alkyl)piperazine, thereby allowing to react at 10° C. to 4000, but is not limited thereto, and may be carried out by using and/or modifying reactions known in the art without limitation.

Meanwhile, in the preparation method of the present invention, the diethyl (hydroxyphenylsulfonyl)methylphosphonate used as the reactant in the Step a-2 and Step b-1 may be prepared through:

Step c-1 of reacting diethyl hydroxymethylphosphonate with toluenesulfonyl halide to prepare (diethoxyphosphoryl) methyl methyl benzenesulfonate;

Step c-2 of reacting (diethoxyphosphoryl)methyl methyl benzenesulfonate with mercaptophenol to prepare (hydroxyphenylthio)methylphosphonate; and Step c-2 of adding meta-chloroperoxybenzoic acid (mCPBA) to (hydroxyphenylthio)methylphosphonate at 0° C., and then allowing to react while stirring at room temperature, but is not limited thereto. For example, commercially available products may be purchased and used, or those synthesized by using and/or modifying methods known in the art may be used without limitation.

Additionally, in order to increase the efficiency and/or yield of the reaction, after each step and before proceeding to the next step, the preparation method of the present invention may further include sequentially carrying out a separation step or a purification step of the selectively produced compound, or both. The separation and/or purification steps may be selectively included or not included in consideration of the reaction conditions of the preceding and subsequent steps and/or substances involved therein.

For example, in the preparation method of the present invention, each step may be carried out in a solution dissolved in an organic solvent selected from the group consisting of methylene chloride (MC or dichloromethane (DCM)), dimethylformamide (DMF), acetonitrile (ACN or MeCN), ethanol, and tetrahydrofuran (THF).

The third aspect of the present invention provides an Nrf2 activator including the compound of the first aspect or a pharmaceutically acceptable salt thereof as an active ingredient.

The fourth aspect of the present invention provides a pharmaceutical composition for preventing or treating diseases induced by a decrease in Nrf2 activity, including the compound of the first aspect or a pharmaceutically acceptable salt thereof as an active ingredient.

The compound of the present invention has the effect of activating Nrf2, which regulates the response to oxidative stress by acting on an antioxidant defense mechanism. Therefore, it can be used as an Nrf2 activator, and further, it can be used for the prevention or treatment of diseases induced by a decrease in Nrf2 activity.

As used herein, the term "nuclear factor erythroid-derived 2-related factor 2 (Nrf2)", which is a transcription factor encoded by the NFE2L2 gene in humans, is a basic leucine zipper protein (bZIP) that regulates the expression of antioxidant proteins that protect against oxidative damage caused by damage or inflammation. Accordingly, drugs that activate the Nrf2 pathway are being studied for the treatment of diseases caused by oxidative stress.

As used herein, the term "prevention" refers to all actions that suppress or delay the onset, spread, and recurrence of the diseases induced by a decrease in Nrf2 activity by administration of the composition of the present invention. Additionally, as used herein, the term "treatment" refers to all actions that alleviate or beneficially change the symptoms of the above diseases by the administration of the composition of the present invention.

As described above, Nrf2 targeted by the compound of the present invention has been reported to be involved in the prevention and treatment of various diseases through an antioxidant defense mechanism by its activation (O. Al-Sawaf et al, *Clinical Science*, 2015, 129:989-999). For example, non-limiting examples of diseases induced by a decrease in Nrf2 activity that can be prevented or treated by administering the composition of the present invention may include liver diseases such as alcoholic liver disease, non-alcoholic liver disease, non-alcoholic fatty liver disease (NAFLD), chronic liver injury, viral hepatitis, and hepatocellular carcinoma; kidney diseases such as diabetic nephropathy, focal segmental glomerulosclerosis, renal fibrosis, lupus-like autoimmune nephritis, chronic kidney disease (CKD), and hypertensive kidney disease; pulmonary diseases such as chronic obstructive pulmonary disease (COPD), pulmonary emphysema, ventilation-associated lung injury, acute lung injury (ALI), acute respiratory distress syndrome (ARDS), pulmonary artery hypertension (PAH), and right heart failure induced by pulmonary artery hypertension; neurodegenerative diseases such as Parkinson's disease (PD), Alzheimer's disease (AD), Huntington's disease, Lou Gehrig's disease, epilepsy, depression, insomnia, anxiety, and multiple sclerosis (MS); mitochondrial myopathy; Friedreich's ataxia; corneal endothelial cell loss; or psoriasis.

The composition of the present invention may further include a pharmaceutically acceptable carrier, a diluent, or an excipient, and may be prepared into various formulations including oral formulations such as a powder, a granule, a tablet, a capsule, a suspension, an emulsion, a syrup, an aerosol, etc., and an injection of sterile injectable solution, etc. according to conventional methods depending on the desired purpose, and the composition may be administered through various routes including oral administration or intravenous, intraperitoneal, subcutaneous, rectal, topical administration, etc. Examples of the appropriate carriers, excipients, and diluents that may be included in the composition may include lactose, dextrose, sucrose, sorbitol, mannitol, xylitol, erythritol, maltitol, starch, acacia rubber, alginate, gelatin, calcium phosphate, calcium silicate, cellulose, methyl cellulose, microcrystalline cellulose, polyvinyl pyrrolidone, water, methylhydroxybenzoate, propylhydroxybenzoate, talc, magnesium stearate, and minerals. Further, the composition of the present invention may further include a filler, an anti-coagulant, a lubricant, a wetting agent, a flavoring agent, an emulsifier, a preservative, etc.

Examples of a solid formulation for oral administration include a tablet, a pill, a powder, a granule a capsule, etc. These solid formulations are prepared by mixing the composition with at least one excipient, for example, starch, calcium carbonate, sucrose, lactose, gelatin, etc. Additionally, a lubricant such as magnesium stearate or talc may also be used in addition to the simple excipient.

Examples of a liquid formulation for oral administration include a suspension, a solution for internal use, an emulsion, a syrup, etc. The liquid formulation may include, in addition to water, a commonly available simple diluent or liquid paraffin, various excipients, such as a wetting agent, a sweetener, an aromatic, a preservative, etc.

A formulation for parenteral administration may include a sterilized aqueous solution, a non-aqueous solvent, a suspension, an emulsion, a lyophilized formulation, and a suppository. As the non-aqueous solvent and the suspension, propylene glycol, polyethylene glycol, a vegetable oil such as olive oil, or an injectable ester such as ethyl oleate may be used. As a base for the suppository formulation, witepsol, macrogol, tween 61, cacao butter, laurin butter, glycerogelatin, etc. may be used. Meanwhile, the injection may include conventional additives such as a solubilizer, an isotonic agent, a suspension, an emulsifier, a stabilizer, a preservative, etc.

The composition of the present invention may be administered in a pharmaceutically effective amount. As used herein, the term "pharmaceutically effective amount" refers to an amount sufficient to treat a disease at a reasonable benefit/risk ratio applicable to any medical treatment without causing an adverse effect, and the effective dosage level may be determined based on the factors including the heath condition of a patient, the type and severity of a disease, the activity of a drug, the sensitivity to a drug, an administration method, an administration time, an administration route and an excretion rate, a duration of treatment, drugs used simultaneously or in combination, and other factors well known in the medical field. The composition of the present invention may be administered as an individual therapeutic agent or in combination with other therapeutic agents, and may be administered sequentially or simultaneously with conventional therapeutic agent, or may be subjected to single or multiple administration. In view of all of the above elements, it is important to administer the composition at a dose in which the maximum effect can be achieved with the minimum amount without adverse effects. Thus, the dose of the composition may be easily determined by those skilled in the art.

However, the dose may be increased or decreased depending on a route of administration, the severity of a disease, the gender, body weight, or age of a patient, etc., and thus, the dose is not intended to limit the scope of the present invention in any way.

Further, the fifth aspect of the present invention provides a method for preventing or treating diseases induced by a decrease in Nrf2 activity in an individual, including administering the pharmaceutical composition of the fourth aspect to an individual in need.

As used herein, the term "subject" refers to all animals including a human, monkey, cow, horse, sheep, pig, chicken, turkey, quail, cat, dog, mouse, rat, rabbit, or guinea pig having the diseases induced by a decrease in Nrf2 activity or being at risk of having such diseases, and the diseases may be effectively prevented or treated by administering the pharmaceutical composition of the present invention to an individual. Additionally, the pharmaceutical composition of the present invention exhibits a therapeutic effect through Nrf2 activation, and thus, it can exhibit a synergistic effect by administering in combination with a conventional therapeutic agent.

As used herein, the term "administration" refers to the introduction of a predetermined substance to a patient by any appropriate method. Regarding the route of administration of the composition of the present invention, the composition may be administered via any common route as long as it can reach a desired tissue. The composition of the present invention may be administered via an intraperitoneal route, an intravenous route, an intramuscular route, a subcutaneous route, an intradermal route, an oral route, a topical route, an intranasal route, an intrapulmonary route, or an intrarectal route, but is not limited thereto. In addition, the pharmaceutical composition may be administered by any device capable of delivering the active component to a target cell. The preferable administration routes and formulations include an intravenous injection, a subcutaneous injection, an intradermal injection, an intramuscular injection, an instillation (injection by drops), etc. The injections may be prepared using aqueous solutions such as saline, Ringer's solution etc., and non-aqueous solutions such as vegetable oils, higher fatty acid esters (e.g., ethyl oleate, etc.), and alcohols (e.g., ethanol, benzyl alcohol, propylene glycol, glycerin, etc.), and may include a pharmaceutical carrier such as a stabilizer for preventing denaturation (e.g., ascorbic acid, sodium bisulfite, sodium pyrosulfite, BHA, tocopherol, EDTA, etc.), an emulsifier, a buffer for pH control, and a preservative for blocking microbial growth (e.g., phenylmercuric nitrate, thiomersal, benzalkonium chloride, phenol, cresol, benzyl alcohol, etc.).

As used herein, the term "therapeutically effective amount" used in combination with the active component refers to the amount of the halo-(3-(phenylsulfonyl)prop-1-enyl)pyridine derivative compound, a tautomer thereof, or a pharmaceutically acceptable salt thereof which is effective in preventing or treating the target diseases.

DETAILED DESCRIPTION OF EMBODIMENTS

The present invention will be described in more detail by way of Examples. However, these Examples are provided for illustrative purposes only, and the scope of the invention is not intended to be limited to or by these Examples.

Preparation Example 1: Synthesis of diethyl (hydroxyphenylsulfonyl)methylphosphonate Step 1-1: Synthesis of (diethoxyphosphoryl)methyl 4-methylbenzenesulfonate from diethyl hydroxymethylphosphonate

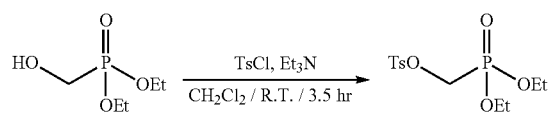 [SMILES: CCOP(=O)(CO)OCC ; CCOP(=O)(COS(=O)(=O)c1ccc(C)cc1)OCC]

(Diethoxyphosphoryl)methyl 4-methylbenzenesulfonate was synthesized according to the reaction scheme above. Specifically, diethyl hydroxymethylphosphonate (10 g, 0.06 mol) was dissolved in methylene chloride (MC), and triethylamine (9.80 mL, 0.07 mmol) and 4-toluenesulfonyl chloride (13.3 g, 0.07 mol) were sequentially added thereto and stirred at room temperature for 3.5 hours. After the reaction was completed, the reaction solution was diluted with ethyl acetate (EtOAc) and washed with water and brine, and then the organic layer was dried over anhydrous $Na_2SO_4$ and filtered. The residue obtained by distilling the solvent under reduced pressure was purified by column chromatography (ethyl acetate:n-hexane=1:3) to obtain (diethoxyphosphoryl) methyl 4-methylbenzenesulfonate (10 g) in a yield of 52%.

Yellow oil;

$R_f$=0.3 (hexane:EtOAc=1:2);

$^1$H NMR (400 MHz, $CDCl_3$): δ 7.80 (d, J=7.6 Hz, 2H), 7.37 (d, J=8.0 Hz, 2H), 4.19-4.12 (m, 6H), 2.46 (s, 3H), 1.31 (t, J=7.4 Hz, 6H).

Step 1-2: Synthesis of diethyl (hydroxyphenylthio)methylphosphonate by Reaction with mercaptophenol

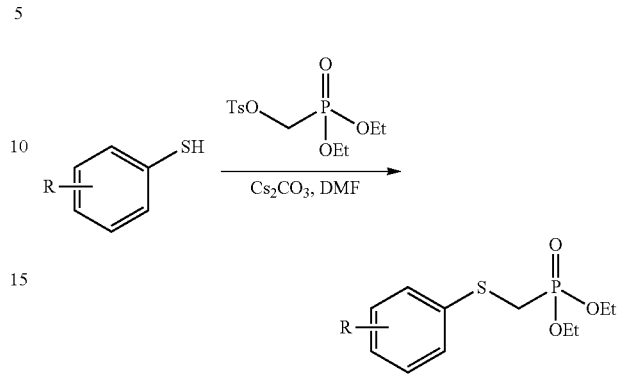

Diethyl (2-, 3-, or 4-substituted phenylthio)methylphosphonate was synthesized according to the reaction scheme above. Specifically, benzenethiol (1.0 eq) in which a fluorine, chlorine, or hydroxy group is substituted at the ortho, meta, or para position was dissolved in dimethylformamide (DMF), and cesium carbonate ($Cs_2CO_3$, 1.2 eq) and the compound (1.2 eq) synthesized in Step 1-1 above were sequentially added thereto and stirred at room temperature for 3.5 hours. After the reaction was completed, the reaction solution was diluted with ethyl acetate (EtOAc) and washed with water and brine, and then the organic layer was dried over anhydrous $Na_2SO_4$ and filtered. The residue obtained by distilling the solvent under reduced pressure was purified by column chromatography (ethyl acetate:n-hexane=3:1) to obtain diethyl (2-, 3-, or 4-substituted phenylthio)methylphosphonate (1-2a to 1-2i). The yield of each compound and the result of identification thereof by $^1$H NMR are shown below. The types and positions of the substituents are shown in Table 1 below.

TABLE 1

| Category | R | Category | R | Category | R |
|---|---|---|---|---|---|
| 1-2a | Ortho-F | 1-2b | Meta-F | 1-2c | Para-F |
| 1-2d | Ortho-Cl | 1-2e | Meta-Cl | 1-2f | Para-Cl |
| 1-2g | Ortho-OH | 1-2h | Meta-OH | 1-2i | Para-OH |

*Diethyl (2-fluorophenylthio)methylphosphonate (1-2a)
Colorless oil;
Yield: 83%;
$R_f$=0.30 (hexane:EtOAc=1:3);
$^1$H NMR (400 MHz, DMSO): δ 1.18 (t, J=6.9 Hz, 6H), 3.43 (d, J=13.8 Hz, 2H), 3.97-4.04 (m, 4H), 7.18-7.59 (m, 4H).

*Diethyl (3-fluorophenylthio)methylphosphonate (1-2b)
Colorless oil;
Yield: 86%;
$R_f$=0.35 (hexane:EtOAc=1:1);
$^1$H NMR (400 MHz, DMSO): δ 1.20 (t, J=7.0 Hz, 6H), 3.52 (d, J=14.1 Hz, 2H), 3.99-4.06 (m, 4H), 7.00-7.37 (m, 4H).

*Diethyl (4-fluorophenylthio)methylphosphonate (1-2c)
Yield: 62%;
$R_f$=0.45 (hexane:EtOAc=1:2);
$^1$H NMR (400 MHz, DMSO): δ 1.19 (t, J=7.0 Hz, 6H), 3.42 (d, J=13.7 Hz, 2H), 3.96-4.03 (m, 4H), 7.16-7.52 (m, 4H).

*Diethyl (2-chlorophenylthio)methylphosphonate (1-2d)
Yield: 80%;
$R_f$=0.37 (hexane:EtOAc=1:2);
$^1$H NMR (400 MHz, DMSO): δ 1.21 (t, J=7.0 Hz, 6H), 3.52 (d, J=14.7 Hz, 2H), 4.01-4.08 (m, 4H), 7.22 (dt, J=1.2 Hz, 7.6 Hz, 1H), 7.34 (dt, J=1.0 Hz, 7.2 Hz, 1H), 7.46 (dd, J=0.9 Hz, 7.9 Hz, 1H), 7.53 (dd, J=1.0 Hz, 7.9 Hz, 1H).

*Diethyl (3-chlorophenylthio)methylphosphonate (1-2e)
Yield: 90%;
$R_f$=0.30 (hexane:EtOAc=1:2);
$^1$H NMR (400 MHz, DMSO): δ 1.20 (t, J=7.0 Hz, 6H), 3.54 (d, J=14.0 Hz, 2H), 4.01-4.05 (m, 4H), 7.25-7.53 (m, 4H).

*Diethyl (4-chlorophenylthio)methylphosphonate (1-2f)
Yield: 94%;
$R_f$=0.33 (hexane:EtOAc=1:3);
$^1$H NMR (400 MHz, DMSO): δ 1.20 (t, J=7.0 Hz, 6H), 3.47 (d, J=13.9 Hz, 2H), 3.99-4.06 (m, 4H), 7.37 (d, J=8.6 Hz, 2H), 7.46 (d, J=19.6 Hz, 2H).

*Diethyl (2-hydroxyphenylthio)methylphosphonate (1-2g)
Yield: 58%;
$R_f$=0.45 (hexane:EtOAc=1:3);
$^1$H NMR (400 MHz, DMSO): δ 1.19 (t, J=7.0 Hz, 6H), 3.29 (d, J=14.8 Hz, 2H), 3.96-4.03 (m, 4H), 6.75-6.83 (m, 1H), 7.06 (t, J=7.6 Hz, 2H), 7.29 (d, J=7.8 Hz, 1H), 9.97 (s, 1H).

*Diethyl (3-hydroxyphenylthio)methylphosphonate (1-2h)
Yield: 87%;
$R_f$=0.33 (hexane:EtOAc=1:3);
$^1$H NMR (400 MHz, DMSO): δ 1.20 (t, J=7.0 Hz, 6H), 3.37 (d, J=14.2 Hz, 2H), 3.98-4.05 (m, 4H), 6.60 (dd, J=8.1 Hz, 1.8 Hz, 1H), 6.79-6.80 (m, 1H), 6.82 (d, J=7.9 Hz, 1H), 7.11 (t, J=7.9 Hz, 1H), 9.58 (s, 1H).

*Diethyl (4-hydroxyphenylthio)methylphosphonate (1-2i)
Yield: 58%;
$R_f$=0.22 (hexane:EtOAc=1:3);
$^1$H NMR (400 MHz, DMSO): δ 1.18 (t, J=7.0 Hz, 6H), 3.23 (d, J=13.5 Hz, 2H), 3.93-4.01 (m, 4H), 6.72 (d, J=8.6 Hz, 2H), 7.31 (d, J=8.6 Hz, 2H), 9.62 (s, 1H).

Step 1-3: Synthesis of diethyl (substituted phenyl-sulfonyl)methylphosphonate by Oxidation Using mCPBA

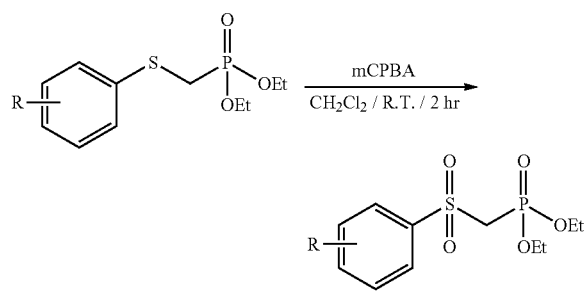

Diethyl (substituted phenyl-sulfonyl)methylphosphonate was synthesized according to the reaction scheme above. Specifically, Compounds 1-2a to 1-2i (1.0 eq) synthesized in Step 1-2 were dissolved in methylene chloride, and meta-chloroperoxybenzoic acid (mCPBA, 2.2 eq) was added thereto at 0° C. and stirred at room temperature for 2 hours. After the reaction was terminated with sodium sulfite, the reaction solution was diluted with ethyl acetate and washed with a saturated aqueous sodium bicarbonate solution. The organic layer was dried over anhydrous $Na_2SO_4$ and filtered, and the residue obtained by distilling the solvent under reduced pressure was purified by column chromatography (ethyl acetate:n-hexane=1:1 to 1:3) to obtain diethyl (2-, 3-, or 4-substituted phenyl-sulfonyl)methylphosphonate (1-3a to 1-3i). The yield of each compound and the result of identification thereof by $^1$H NMR are shown below. The types and positions of the substituents are shown in Table 2 below.

TABLE 2

| Category | R | Category | R | Category | R |
| --- | --- | --- | --- | --- | --- |
| 1-3a | Ortho-F | 1-3b | Meta-F | 1-3c | Para-F |
| 1-3d | Ortho-Cl | 1-3e | Meta-Cl | 1-3f | Para-Cl |
| 1-3g | Ortho-OH | 1-3h | Meta-OH | 1-3i | Para-OH |

*Diethyl (2-fluorophenylsulfonyl)methylphosphonate (1-3a)
Colorless oil:
Yield: 60%;
$R_f$=0.53 (hexane:EtOAc=1:3);
$^1$H NMR (400 MHz, CDCl$_3$): δ 1.15 (t, J=7.0 Hz, 6H), 3.96-4.02 (m, 4H), 4.44 (d, J=17.0 Hz, 2H), 7.45-7.88 (m, 4H).

*Diethyl (3-fluorophenylsulfonyl)methylphosphonate (1-3b)
Colorless oil;
Yield: 98%;
$R_f$=0.53 (hexane:EtOAc=1:3);
$^1$H NMR (400 MHz, DMSO): δ 1.16 (t, J=7.0 Hz, 6H), 3.93-4.06 (m, 4H), 4.55 (d, J=17.0 Hz, 2H), 7.52-7.81 (m, 4H).

*Diethyl (4-fluorophenylsulfonyl)methylphosphonate (1-3c)
Colorless oil:
Yield: 100%;
$R_f$=0.28 (hexane:EtOAc=1:7);
$^1$H NMR (400 MHz, DMSO): δ 1.16 (t, J=7.0 Hz, 6H), 3.94-4.03 (m, 4H), 4.49 (d, J=16.9 Hz, 2H), 7.50 (t, J=8.8 Hz, 2H), 7.99-8.03 (m, 4H).

*Diethyl (2-chlorophenylsulfonyl)methylphosphonate (1-3d)
Colorless oil;
Yield: 99%;
$R_f$=0.34 (hexane:EtOAc=1:3);
$^1$H NMR (400 MHz, DMSO): δ 1.14 (t, J=7.0 Hz, 6H), 3.94-4.02 (m, 4H), 4.50 (d, J=17.0 Hz, 2H), 7.62-7.76 (m, 3H), 8.03 (d, J=7.8 Hz, 1H).

*Diethyl (3-chlorophenylsulfonyl)methylphosphonate (1-3e)
Colorless oil;
Yield: 90%;
$R_f$=0.34 (hexane:EtOAc=1:3);
$^1$H NMR (400 MHz, DMSO): δ 1.16 (t, J=7.0 Hz, 6H), 3.96-4.04 (m, 4H), 4.56 (d, J=17.0 Hz, 2H), 7.69 (t, J=7.9 Hz, 1H), 7.83 (d, J=8.0 Hz, 1H), 7.90 (d, J=8.0 Hz, 1H), 7.99 (s, 1H).

*Diethyl (4-chlorophenylsulfonyl)methylphosphonate (1-3f)
Colorless oil;
Yield: 90%;
$R_f$=0.34 (hexane:EtOAc=1:5);

$^1$H NMR (400 MHz, DMSO): δ 1.17 (t, J=6.8 Hz, 6H), 3.98-4.02 (m, 4H), 4.52 (d, J=16.9 Hz, 2H), 7.74 (d, J=7.4 Hz, 1H), 7.96 (d, J=7.4 Hz, 1H).

*Diethyl (2-hydroxyphenylsulfonyl)methylphosphonate (1-3g)

Colorless oil;
Yield: 69%;
$R_f$=0.22 (hexane:EtOAc=1:7);
$^1$H NMR (400 MHz, DMSO): δ 1.14 (t, J=7.0 Hz, 6H), 3.89-4.03 (m, 4H), 4.33 (d, J=16.7 Hz, 2H), 6.96-7.04 (m, 2H), 7.51 (t, J=7.4 Hz, 1H), 7.67 (d, J=7.9 Hz, 1H), 11.25 (s, 1H).

*Diethyl (3-hydroxyphenylsulfonyl)methylphosphonate (1-3h)

Colorless oil;
Yield: 84%;
$R_f$=0.22 (hexane:EtOAc=1:7);
$^1$H NMR (400 MHz, DMSO): δ 1.16 (t, J=7.0 Hz, 6H), 3.93-4.03 (m, 4H), 4.37 (d, J=17.0 Hz, 2H), 7.09 (d, J=7.9 Hz, 1H), 7.29-7.45 (m, 3H), 10.25 (s, 1H).

*Diethyl (4-hydroxyphenylsulfonyl)methylphosphonate (1~3i)

Colorless oil;
Yield: 95%;
$R_f$=0.21 (hexane:EtOAc=1:7);
$^1$H NMR (400 MHz, DMSO): δ 1.16 (t, J=7.0 Hz, 6H), 392-4.04 (m, 4H), 4.28 (d, J=16.9 Hz, 2H), 6.93, 7.74 (d, J=8.7 Hz, 4H), 10.60 (s, 1H).

Example 1: Synthesis of (E)-3-fluoro-2-(2-(2-fluorophenylsulfonyl)vinyl)pyridine (Compound 1)

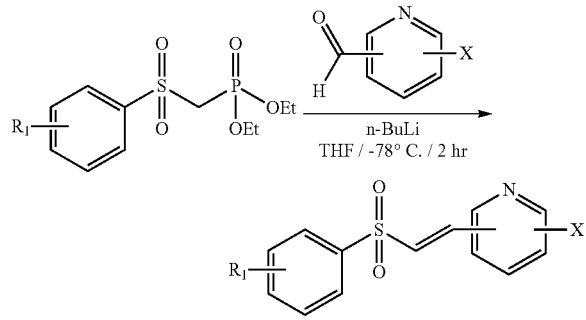

After dissolving diethyl (2-fluorophenylsulfonyl)methylphosphonate (1-3a, 1 eq) prepared according to Preparation Example 1 in anhydrous THF (0.1 M), the reaction mixture was cooled to −78° C. using dry ice and acetone. n-BuLi (1.2 eq, 2.0 M cyclohexane solution) was slowly added dropwise to the solution and stirred for 1 hour, and then 3-fluoropicolinaldehyde (1.2 eq) was added and reacted again for another hour. If the reaction had not completed when confirmed by TLC, the reaction was carried out for another 30 minutes at room temperature. After the reaction was terminated with a small amount of water, the reaction mixture was extracted with water and 10% MeOH/MC, a small amount of water was removed from the organic layer using anhydrous Na$_2$SO$_4$, and the solvent was removed by distillation under reduced pressure and vacuum-dried. Thereafter, the products were separated and purified by column chromatography using EtOAc and 10% MeOH/MC to obtain (E)-3-fluoro-2-(2-(2-fluorophenylsulfonyl)vinyl)pyridine.

Yield: 71%;
$R_f$=0.33 (2% MeOH/MC);
$^1$H NMR (400 MHz, DMSO): δ 7.50-8.00 (m, 6H, 2 trans H), 8.54 (d, J=4.1 Hz, 1H);
$^{13}$C NMR (100 MHz, CDCl$_3$): δ 117.2 (d, $J_{C-F}$=20.7 Hz), 124.2 (d, $J_{C-F}$=18.9 Hz), 124.8 (d, $J_{C-F}$=3.7 Hz), 126.9 (d, $J_{C-F}$=4.4 Hz), 128.2 (d, $J_{C-F}$=13.9 Hz), 129.9, 132.2 (d, $J_{C-F}$=3.3 Hz), 135.0, 136.2 (d, $J_{C-F}$=8.5 Hz), 139.5 (d, $J_{C-F}$=11.0 Hz), 146.0 (d, $J_{C-F}$=5.0 Hz), 158.5 (d, $J_{C-F}$=264.3 Hz), 159.7 (d, $J_{C-F}$=255.6 Hz).

Example 2: Synthesis of (E)-3-fluoro-2-(2-(3-fluorophenylsulfonyl)vinyl)pyridine (Compound 2)

The reaction was performed in the same manner as in Example 1 to obtain (E)-3-fluoro-2-(2-(3-fluorophenylsulfonyl)vinyl)pyridine, except that diethyl (3-fluorophenylsulfonyl)methylphosphonate (1-3b) was used instead of diethyl (2-fluorophenylsulfonyl)methylphosphonate (1-3a).

Yield: 62%;
$R_f$=0.41 (hexane:EtOAc=1:1);
$^1$H NMR (300 MHz, DMSO): δ 7.60-7.93 (m, 8H, 2 trans H), 8.52-8.54 (m, 1H);
$^{13}$C NMR (75 MHz, DMSO): δ 114.7 (d, $J_{C-F}$=24.4 Hz), 121.2 (d, $J_{C-F}$ 21.1 Hz), 123.8 (d, $J_{C-F}$=3.0 Hz), 124.8 (d, $J_{C-F}$=18.8 Hz), 128.0 (d, $J_{C-F}$=4.7 Hz), 132.1 (d, $J_{C-F}$=13.5 Hz), 132.1, 133.7, 138.4 (d, $J_{C-F}$=10.9 Hz), 141.7 (d, $J_{C-F}$ 6.7 Hz), 146.3 (d, $J_{C-F}$=4.8 Hz), 158.3 (d, $J_{C-F}$=288.2 Hz), 161.7 (d, $J_{C-F}$=273.9 Hz).

Example 3: Synthesis of (E)-3-fluoro-2-(2-(4-fluorophenylsulfonyl)vinyl)pyridine (Compound 3)

The reaction was performed in the same manner as in Example 1 to obtain (E)-3-fluoro-2-(2-(4-fluorophenylsulfonyl)vinyl)pyridine, except that diethyl (4-fluorophenylsulfonyl)methylphosphonate (1-3c) was used instead of diethyl (2-fluorophenylsulfonyl)methylphosphonate (1-3a).

Yield: 81%;
$R_f$=0.42 (hexane:EtOAc=1:1);
$^1$H NMR (300 MHz, DMSO): δ 7.59-7.92 (n, 8H, 2 trans H), 8.51-8.53 (m, 1H);
$^{13}$C NMR (75 MHz, DMSO): δ 114.7 (d, $J_{C-F}$=24.4 Hz), 121.2 (d, $J_{C-F}$ 21.1 Hz), 123.8 (d, $J_{C-F}$=3.0 Hz), 124.8 (d, $J_{C-F}$=18.9 Hz), 128.0 (d, $J_{C-F}$=4.8 Hz), 132.1 (d, $J_{C-F}$=13.7 Hz), 132.1, 133.7, 138.4 (d, $J_{C-F}$=10.9 Hz), 141.7 (d, $J_{C-F}$=6.7 Hz), 146.3 (d, $J_{C-F}$=4.8 Hz), 158.3 (d, $J_{C-F}$=288.1 Hz), 161.7 (d, $J_{C-F}$=273.9 Hz).

Example 4: Synthesis of (E)-3-chloro-2-(2-(2-fluorophenylsulfonyl)vinyl)pyridine (Compound 4)

The reaction was performed in the same manner as in Example 1 to obtain (E)-3-chloro-2-(2-(2-fluorophenylsulfonyl)vinyl)pyridine, except that 3-chioropicolinaldehyde was used instead of 3-fluoropicolinaldehyde.

Yield: 90%;
$R_f$=0.37 (hexane:EtOAc=2:1);
$^1$H NMR (400 MHz, DMSO): δ 7.50-7.57 (m, 3H), 7.75 (d, J=14.7 Hz, trans H), 7.83-7.98 (m, 2H), 8.02 (d, J=15.0 Hz, trans H), 8.09 (d, J=8.2 Hz, 1H), 8.63 (d, J=4.4 Hz, 1H);
$^{13}$C NMR (100 MHz, DMSO): δ 118.0 (d, $J_{C-F}$=20.6 Hz), 126.1 (d, $J_{C-F}$ 3.5 Hz), 127.6 (d, $J_{C-F}$=13.8 Hz), 127.8, 130.1, 132.8, 133.4, 137.4, 137.8 (d, $J_{C-F}$=8.6 Hz), 138.9, 147.1, 149.1, 159.2 (d, $J_{C-F}$=253.1 Hz).

Example 5: Synthesis of (E)-3-chloro-2-(2-(3-fluorophenylsulfonyl)vinyl)pyridine (Compound 5)

The reaction was performed in the same manner as in Example 2 to obtain (E)-3-chloro-2-(2-(3-fluorophenylsulfonyl)vinyl)pyridine, except that 3-chloropicolinaldehyde was used instead of 3-fluoropicolinaldehyde.

Yield: 68%;
$R_f$=0.27 (hexane:EtOAc=2:1);
$^1$H NMR (300 MHz, DMSO): δ 7.53-8.10 (m, 8H, 2 trans H), 8.61 (dd, J=1.2, 4.5 Hz, 1H);
$^{13}$C NMR (75 MHz, DMSO): δ 114.7 (d, $J_{C-F}$=24.4 Hz), 121.3 (d, $J_{C-F}$ 21.2 Hz), 123.8 (d, $J_{C-F}$=3.1 Hz), 127.1, 132.1 (d, $J_{C-F}$=7.9 Hz), 132.3, 133.3, 135.9, 1384, 141.6 (d, $J_{C-F}$=6.7 Hz), 146.8, 148.5, 161.9 (d, $J_{C-F}$=248.0 Hz).

Example 6: Synthesis of (E)-3-chloro-2-(2-(4-fluorophenylsulfonyl)vinyl)pyridine (Compound 6)

The reaction was performed in the same manner as in Example 3 to obtain (E)-3-chloro-2-(2-(4-fluorophenylsulfonyl)vinyl)pyridine, except that 3-chloropicolinaldehyde was used instead of 3-fluoropicolinaldehyde.

Yield: 58%;
$R_f$=0.36 (hexane:EtOAc=2:1);
$^1$H NMR (300 MHz, DMSO): δ 7.49-7.55 (m, 3H), 7.87 (dd, J=14.8 Hz, 14.8 Hz, 2 trans H), 8.06-8.11 (m, 3H), 8.60 (d, J=4.5 Hz, 1H);
$^{13}$C NMR (75 MHz, DMSO): δ 116.8, 117.1, 127.0, 130.9, 131.0, 132.2, 133.9, 135.1, 135.8 (d, $J_{C-F}$=2.8 Hz), 138.36, 146.91, 148.54, 165.17 (d, $J_{C-F}$=251.8 Hz).

Example 7: Synthesis of (E)-2-(2-(2-chlorophenylsulfonyl)vinyl)-3-fluoropyridine (Compound 7)

The reaction was performed in the same manner as in Example 1 to obtain (E)-2-(2-(2-chlorophenylsulfonyl)vinyl)-3-fluoropyridine, except that diethyl (2-chlorophenylsulfonyl)methylphosphonate (1-3d) was used instead of diethyl (2-fluorophenylsulfonyl)methylphosphonate (1-3a).

Yield: 75%;
$R_f$=0.34 (hexane:EtOAc=2:1);
$^1$H NMR (400 MHz, DMSO): δ 7.62-7.93 (m, 7H), 8.18 (dd, J=1.4 Hz, 7.8 Hz, 1H), 8.55 (d, J=4.4 Hz, 1H);
$^{13}$C NMR (100 MHz, DMSO): δ 125.4 (d, $J_{C-F}$=18.9 Hz), 128.7 (d, $J_{C-F}$=4.7 Hz), 128.9, 131.2, 131.3 (d, $J_{C-F}$=4.3 Hz), 131.9, 132.6, 135.8, 136.3, 137.2, 138.7 (d, $J_{C-F}$=10.9 Hz), 147.0 (d, $J_{C-F}$=4.7 Hz), 158.7 (d, $J_{C-F}$=262.0 Hz).

Example 8: Synthesis of (E)-2-(2-(3-chlorophenylsulfonyl)vinyl)-3-fluoropyridine (Compound 8)

The reaction was performed in the same manner as in Example 1 to obtain (E)-2-(2-(3-chlorophenylsulfonyl)vinyl)-3-fluoropyridine, except that diethyl (3-chlorophenylsulfonyl)methylphosphonate (1-3e) was used instead of diethyl (2-fluorophenylsulfonyl)methylphosphonate (1-3a).

Yield: 97%;
Rt=0.38 (hexane:EtOAc=2:1);
$^1$H NMR (400 MHz, DMSO): δ 7.60-7.92 (m, 7H), 7.98 (d, J=7.8 Hz, 1H), 8.08-8.09 (m, 1H), 8.52 (d, J=4.4 Hz, 1H);
$^{13}$C NMR (100 MHz, DMSO): δ 124.8 (d, $J_{C-F}$=18.8 Hz), 126.3, 127.3, 128.0 (d, $J_{C-F}$=4.6 Hz), 131.6, 132.2 (d, $J_{C-F}$=4.1 Hz), 133.9, 134.2 (d, $J_{C-F}$=12.2 Hz), 134.2, 138.4 (d, $J_{C-F}$=10.9 Hz), 141.6, 146.3 (d, $J_{C-F}$=4.7 Hz), 158.1 (d, $J_{C-F}$=262.1 Hz).

Example 9: Synthesis of (E)-2-(2-(4-chlorophenylsulfonyl)vinyl)-3-fluoropyridine (Compound 9)

The reaction was performed in the same manner as in Example 1 to obtain (E-2-(2-(4-chlorophenylsulfonyl)vinyl)-3-fluoropyridine, except that diethyl (4-chlorophenylsulfonyl)methylphosphonate (1-3f) was used instead of diethyl (2-fluorophenylsulfonyl)methylphosphonate (1-3a).

Yield: 70%;
$R_f$=0.32 (hexane:EtOAc=3:1);
$^1$H NMR (400 MHz, DMSO): δ 7.59-7.76 (m, 5H), 7.88 (t, J=9.2 Hz, 1H), 8.02 (d, J=8.6 Hz, 2H), 8.52 (d, J=4.4 Hz, 1H);
$^{13}$C NMR (100 MHz, DMSO): δ 124.8 (d, $J_{C-F}$=18.8 Hz), 128.0 (d, $J_{C-F}$ 4.7 Hz), 129.6, 129.8, 132.5 (d, $J_{C-F}$=4.2 Hz), 133.3, 138.4, 138.5, 139.1, 146.4 (d, $J_{C-F}$=4.8 Hz), 158.1 (d, $J_{C-F}$=262.0 Hz).

Example 10: Synthesis of (E)-3-chloro-2-(2-(2-chlorophenylsulfonyl)vinyl)pyridine (Compound 10)

The reaction was performed in the same manner as in Example 7 to obtain (E)-3-chloro-2-(2-(2-chlorophenylsulfonyl)vinyl)pyridine, except that 3-chloropicolinaldehyde was used instead of 3-fluoropicolinaldehyde.

Yield: 70%;
$R_f$=0.37 (hexane:EtOAc=2:1);
$^1$H NMR (400 MHz, DMSO): δ 7.54-8.10 (m, 7H), 8.17 (d, J=7.8 Hz, 1H), 8.63 (d, J=4.4 Hz, 1H);
$^{13}$C NMR (100 MHz, DMSO): δ 127.8, 128.9, 131.3, 131.9, 132.5, 132.6, 132.8, 136.4, 137.1, 138.3, 138.9, 147.2, 149.2.

Example 11: Synthesis of (E)-3-chloro-2-(2-(3-chlorophenylsulfonyl)vinyl)pyridine (Compound 11)

The reaction was performed in the same manner as in Example 8 to obtain (E)-3-chloro-2-(2-(3-chlorophenylsulfonyl)vinyl)pyridine, except that 3-chloropicolinaldehyde was used instead of 3-fluoropicolinaldehyde.

Yield: 71%;
$R_f$=0.50 (hexane:EtOAc=2:1);
$^1$H NMR (400 MHz, DMSO): δ 7.53 (m, 1H), 7.70 (t, J=7.9 Hz, 1H), 7.84-8.07 (m, 6H), 8.60 (d, J=4.0 Hz, 1H);
$^{13}$C NMR (100 MHz, DMSO): δ 126.8, 127.6, 127.8, 132.2, 132.8, 133.9, 134.5, 134.8, 136.6, 138.9, 141.9, 147.4, 149.0.

Example 12: Synthesis of (E)-3-chloro-2-(2-(4-chlorophenylsulfonyl)vinyl)pyridine (Compound 12)

The reaction was performed in the same manner as in Example 9 to obtain (E)-3-chloro-2-(2-(4-chlorophenylsulfonyl)vinyl)pyridine, except that 3-chloropicolinaldehyde was used instead of 3-fluoropicolinaldehyde.

Yield: 70%;
$R_f$=0.40 (hexane:EtOAc=3:1);
$^1$H NMR (400 MHz, DMSO): δ 7.53-7.77 (m, 3H), 7.81 (t, J=14.8 Hz, trans H), 7.96 (d, J=14.7 Hz, trans H), 8.02 (d, J=7.2 Hz, 2H), 8.07 (d, J=8.2 Hz, 1H), 8.61 (d, J=4.4 Hz, 1H);
$^{13}$C NMR (100 MHz, DMSO): δ 127.6, 130.1, 130.3, 132.8, 134.2, 136.1, 138.8, 138.9, 1397, 147.4, 149.0.

Example 13: Synthesis of (E)-2-chloro-6-(2-(2-chlorophenylsulfonyl)vinyl)pyridine (Compound 13)

The reaction was performed in the same manner as in Example 10 to obtain (E)-2-chloro-6-(2-(2-chlorophenylsulfonyl)vinyl)pyridine, except that 6-chloropicolinaldehyde was used instead of 3-chloropicolinaldehyde.

Yield: 94%;
$R_f$=0.30 (hexane EtOAc=1:1);
$^1$H NMR (400 MHz, DMSO): δ 7.54-7.83 (m, 5H), 7.93 (d, J=15.4 Hz, trans H), 8.18 (dd, J=1.4 Hz, 7.9 Hz, 1H), 8.39 (dd, J=1.7 Hz, 7.8 Hz, 1H), 8.50 (d, J=4.4 Hz, 1H);
$^{13}$C NMR (100 MHz, DMSO): δ 124.3, 127.4, 128.9, 131.2, 131.5, 132.0, 132.6, 1363, 137.2, 138.6, 139.1, 150.8, 152.4.

Example 14: Synthesis of (E)-2-chloro-3-(2-(2-chlorophenylsulfonyl)vinyl)pyridine (Compound 14)

The reaction was performed in the same manner as in Example 10 to obtain (E)-2-chloro-3-(2-(2-chlorophenylsulfonyl)vinyl)pyridine, except that 2-chloronicotinaldehyde was used instead of 3-chloropicolinaldehyde.

Yield: 96%;
$R_f$=0.30 (hexane EtOAc=2:1);
$^1$H NMR (400 MHz, DMSO): δ 7.60 (d, J=7.8 Hz, 1H), 7.66-7.82 (m, 5H), 7.89 (d, J=7.4 Hz, 1H), 7.99 (t, J=7.7 Hz, 1H), 8.16 (dd, J=1.4 Hz, 7.8 Hz, 1H);
$^{13}$C NMR (100 MHz, DMSO): δ 125.5, 126.8, 128.3, 131.1, 131.2, 132.1, 132.6, 136.3, 137.3, 141.6, 142.4, 151.1, 151.6.

Preparation Example 2: Synthesis of diethyl (4-(2-(4-methylpiperazin-1-yl)-2-oxoethoxy)phenylsulfonyl)methylphosphonate by Introduction of piperazinyl Moiety Step 2-1

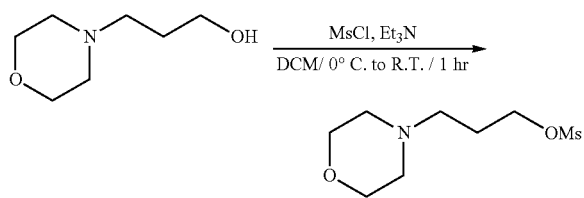

Synthesis of 3-morpholinopropyl methanesulfonate

According to the reaction scheme above, 3-morpholinopropyl methanesulfonate was synthesized. Specifically, 4-(3-hydroxypropyl)morpholine (1 eq, 4.76 mL, 34.43 mmol), a commercially available reagent, was added to a reactor and dissolved with methylene chloride (0.12 M, 280 mL), and then triethylamine (1.2 eq, 5.76 mL, 41.32 mmol) and methanesulfonyl chloride (1.2 eq, 3.2 mL, 41.32 mmol) were added thereto at 0° C. and reacted at room temperature for 1 hour. After the reaction was completed, the reaction solution was extracted with water and 10% MeOH/MC, and a small amount of water was removed from the organic layer using anhydrous MgSO$_4$, and then the solvent was removed by distillation under reduced pressure. Subsequently, the solvent was immediately vacuum-dried without separation and purification by column chromatography to obtain a colorless-brown oil compound, 3-morpholinopropyl methanesulfonate (6.47 g), Crude Yield: 84%;
$^1$H NMR (400 MHz, CDCl$_3$): δ 1.95-1.90 (m, 2H), 2.44 (t, J=6.9 Hz, 6H), 3.00 (s, 3H), 3.68 (t, J=4.6 Hz, 4H), 4.30 (t, J=6.3 Hz, 2H).

Step 2-2: Synthesis of diethyl 3-morpholinopropoxy)phenylsulfonyl)methylphosphonate

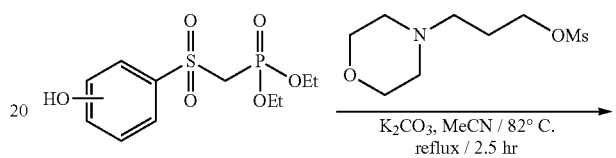

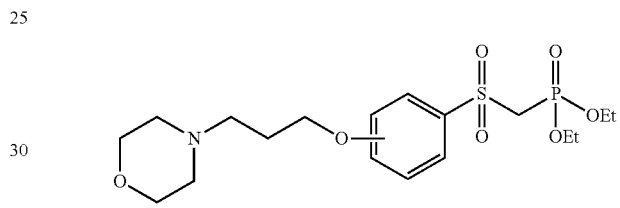

Diethyl (3-morpholinopropoxy)phenylsulfonyl)methylphosphonate was synthesized according to the reaction scheme above. Specifically, Compounds 1-3h and 1-3i (1 eq, 1.03 g, 3.34 mmol) prepared according to Preparation Example 1 were dissolved in acetonitrile (0.1 M, 34 mL), and then potassium carbonate (1.5 eq, 0.69 g, 5.01 mmol) and the compound synthesized from Step 2-1 (1.48 eq, 1.10 g, 4.95 mmol) were added thereto at room temperature and stirred at reflux at 82° C. for 2 hours and 30 minutes. After the reaction was completed, the reaction mixture was cooled to room temperature and extracted with water and 10% MeOH/MC, and a small amount of water was removed from the organic layer using anhydrous Na$_2$SO$_4$, and then the solvent was removed by distillation under reduced pressure and vacuum-dried. Subsequently, the products were separated and purified by column chromatography (100% EtOAc and 10% MeOH/MC) to obtain diethyl (3-(3-morpholinopropoxy)phenylsulfonyl)methylphosphonate and diethyl (4-(3-morpholinopropoxy)phenylsulfonyl)methylphosphonate.

TABLE 3

| category | R$_1$ |
|---|---|
| 2-2a | <br>para- |

TABLE 3-continued

| category | R₁ |
|---|---|
| 2-2b | 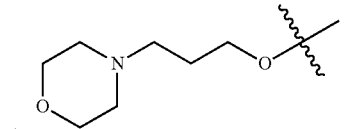 meta- |

Example 15: Synthesis of (E)-4-(3-(4-(2-(3-fluoropyridin-2-yl)vinylsulfonyl)phenoxy)propyl)morpholine hydrochloride (Compound 15)

The reaction was performed in the same manner as in Example 1 to obtain (E)-4-(3-(4-(2-(3-fluoropyridin-2-yl)vinylsulfonyl)phenoxy)propyl)morpholine, except that diethyl (4-(3-morpholinopropoxy)phenylsulfonyl)methylphosphonate (2-2a) was used instead of diethyl (2-fluorophenylsulfonyl)methylphosphonate (1-3a). After dissolving the obtained compound in EtOAc, an excess of HCl (4.0 M 1,4-dioxane solution) was added dropwise, and the reaction mixture was reacted at room temperature for 2 hours. Subsequently, the thus-formed precipitates were filtered while washing several times with hexane and EtOAc, and separated and purified by column chromatography using EtOAc and 10% MeOH/MC to obtain (E)-4-(3-(4-(2-(3-fluoropyridin-2-yl)vinylsulfonyl)phenoxy)propyl)morpholine hydrochloride.

Yield: 97%;
$R_f$=0.35 (MeOH:EtOAc=1:4);
¹H NMR (400 MHz, DMSO): δ 2.18-3.24 (m, 6H), 3.45 (d, J=12.2 Hz, 2H), 3.79 (t, J=11.9 Hz, 2H), 3.95 (d, J=12.2 Hz, 2H), 4.20 (t, J=5.8 Hz, 2H), 7.19 (d, J=8.7 Hz, 2H), 7.57-7.62 (m, 1H), 7.66 (s, 2H), 7.87 (t, J=9.6 Hz, 1H), 7.93 (d, J=8.6 Hz, 2H), 8.50 (d, J=3.8 Hz, 1H), 11.00 (s, 1H);
¹³C NMR (100 MHz, DMSO): 23.2, 51.5, 53.7, 63.6, 66.1, 115.9, 125.3 (d, $J_{C-F}$=9.6 Hz), 128.2, 130.5, 131.7, 132.1, 134.06 (d, $J_{C-F}$=4.2 Hz), 139.10 (d, $J_{C-F}$ 10.9 Hz), 146.87 (d, $J_{C-F}$=4.6 Hz), 158.5 (d, $J_{C-F}$=261.3 Hz), 163.0.

Example 16: Synthesis of (E)-4-(3-(3-(2-(3-fluoropyridin-2-yl)vinylsulfonyl)phenoxy)propyl)morpholine hydrochloride (Compound 16)

The reaction was performed in the same manner as in Example 15 to obtain (E)-4-(3-(3-(2-(3-fluoropyridin-2-yl)vinylsulfonyl)phenoxy)propyl)morpholine hydrochloride, except that diethyl (3-(3-morpholinopropoxy)phenylsulfonyl)methylphosphonate (2-2b) was used instead of diethyl (4-(3-morpholinopropoxy)phenylsulfonyl)methylphosphonate (2-2a).

Yield: 97%;
$R_f$=0.35 (MeOH:EtOAc=1:4);
¹H NMR (400 MHz, CDCl₃): δ 1.95-3.73 (m, 12H), 4.08 (t, J=6.3 Hz, 2H), 7.14 (dd, J=8.2 Hz, 2.1 Hz, 1H), 7.32-7.54 (m, 6H), 7.91 (d, J=15.0 Hz, 1H), 8.42 (d, J=4.4 Hz, 1H), 11.00 (s, 1H);
¹³C NMR (100 MHz, CDCl₃): δ 26.2, 53.7, 55.3, 66.6, 66.9, 112.8, 120.1, 120.6, 124.1 (d, $J_{C-F}$=19.0 Hz), 126.67 (d, $J_{C-F}$=4.4 Hz), 130.5, 132.9, 133.2 (d, $J_{C-F}$=4.4 Hz), 141.1, 145.94 (d, $J_{C-F}$=5.1 Hz), 158.4 (d, $J_{C-F}$=264.1 Hz), 159.6.

Preparation Example 3: Synthesis of diethyl (4-(2-(4-methylpiperazin-1-yl)-2-oxoethoxy)phenylsulfonyl)methylphosphonate by Introduction of piperazinyl Moiety

Step 3-1: Synthesis of ethyl 2-(4-((diethoxyphosphoryl)methylsulfonyl)phenoxyacetate by reaction with ethyl haloacetate

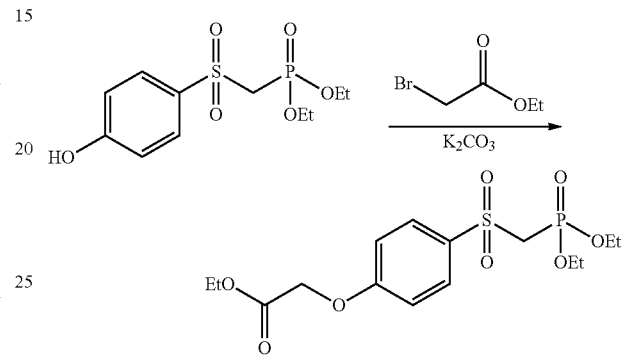

Into a solution prepared by dissolving Compound 1-3i (1 eq, 3.02 g, 9.80 mmol) prepared according to Preparation Example 1 in acetonitrile (ACN, 25 mL), K₂CO₃ (1.5 eq, 2.03 g, 14.70 mmol) and ethyl bromoacetate (1.2 eq, 1.3 mL, 11.70 mmol) were added dropwise at room temperature, and the reaction mixture was heated and stirred at 90° C. for 2 hours. After the reaction was completed, the reaction mixture was cooled to room temperature and extracted with water and 10% MeOH/MC, and a small amount of water was removed from the organic layer using anhydrous MgSO₄, and then the solvent was removed by distillation under reduced pressure and vacuum-dried. Subsequently, the products were separated and purified by column chromatography (ethyl acetate:n-hexane=1:1 to 1:3) to obtain a colorless oil compound, ethyl 2-(4-((diethoxyphosphoryl)methylsulfonyl)phenoxy)acetate (3.88 g).

Yield: 100%;
$R_f$=0.30 (EtOAc:acetone=6:1);
¹H NMR (400 MHz, DMSO): δ 1.18 (t, J=5.7 Hz, 6H), 1.22 (t, J=7.1 Hz, 6H), 3.93-4.03 (m, 4H), 4.18 (q, J=7.1 Hz, 14.2 Hz, 2H), 4.38 (d, J=16.9 Hz, 2H), 4.94 (s, 2H), 7.15 (d, J=8.9 Hz, 2H), 7.85 (d, J=8.9 Hz, 2H).

Step 3-2: Synthesis of ((diethoxyphosphoryl)methylsulfonyl)phenoxy) Acetic Acid by Conversion of Acetate to Acetic Acid

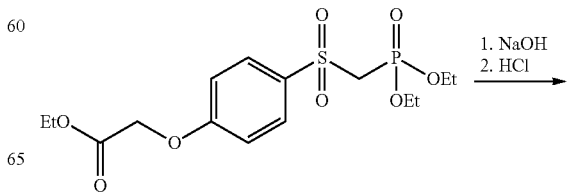

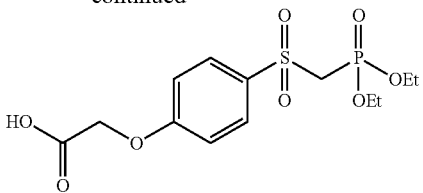

After dissolving the compound (1 eq, 2.0 g, 5.07 mmol) synthesized in Step 3-1 in a NaOH solution (1.5 eq, 0.3 mg, 7.60 mmol) dissolved in ethanol (10 mL), the reaction mixture was reacted at room temperature for 2 hours. After the reaction was completed, the solvent was removed by distillation under reduced pressure. The compound was acidified by adding water and HCl and extracted with EtOAc, and a small amount of water was removed from the organic layer using anhydrous $Na_2SO_4$. Thereafter, the solvent was removed by distillation under reduced pressure, followed by vacuum drying without further separation and purification to obtain a colorless-brown oil compound, 2-(4-((diethoxyphosphoryl)methylsulfonyl)phenoxy)acetic acid (1.83 g).

Yield: 98%;
$R_f$=0.34 (20% MeOH/MC);
$^1$H NMR (400 MHz, DMSO): δ 1.16 (t, J=6.9 Hz, 6H), 3.93-4.01 (m, 4H), 4.37 (d, J=16.9 Hz, 2H), 4.83 (s, 2H), 7.13 (d, J=8.1 Hz, 2H), 7.85 (d, J=8.0 Hz, 2H), 13.20 (s, 1H).

Step 3-3: Synthesis of diethyl (4-(2-(4-methylpiperazin-1-yl)-2-oxoethoxy)phenylsulfonyl)methylphosphonate by Substitution with Piperazinyl Derivatives

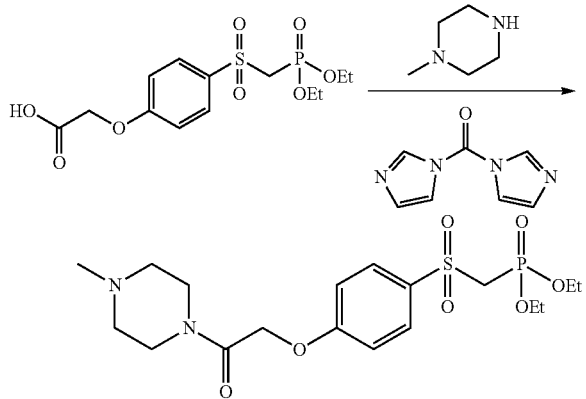

After dissolving the compound (1 eq, 1.82 g, 4.98 mmol) synthesized in Step 3-2 in tetrahydrofuran (THF), 1,1'-carbonyldiimidazole (CDI, 3 eq, 2.42 g, 14.90 mmol) was slowly added dropwise, and the reaction mixture was reacted at room temperature for 20 minutes, and then 1-methylpiperazine (1.2 eq, 0.66 mL, 5.97 mmol) was added dropwise and reacted at room temperature for 2 hours. After the reaction was completed, the solvent was removed by distillation under pressure, and then extracted with EtOAc, and a small amount of water was removed from the organic layer using anhydrous $Na_2SO_4$ and vacuum-dried. Thereafter, the products were separated and purified by column chromatography using MeOH and MC to obtain a colorless oil compound, diethyl (4-(2-(4-methylpiperazin-1-yl)-2-oxoethoxy)phenylsulfonyl)methylphosphonate (1.32 g).

Yield: 60%;
$R_f$=0.33 (10% MeOH/MC);
$^1$H NMR (400 MHz, DMSO): δ 1.16 (t, J=7.0 Hz, 6H), 2.19 (s, 3H), 2.26-2.34 (m, 4H), 3.43-4.01 (m, 8H), 4.10 (q, J=5.3 Hz, 10.5 Hz, 2H), 4.35 (d, J=16.9 Hz, 2H), 4.99 (s, 2H), 7.10 (d, J=8.9 Hz, 2H), 7.83 (d, J=8.9 Hz, 2H).

Example 17: Synthesis of (E)-2-(4-(2-(3-fluoropyridin-2-yl)vinylsulfonyl)phenoxy)-1-(4-methylpiperazin-1-yl)ethanone hydrochloride (Compound 17)

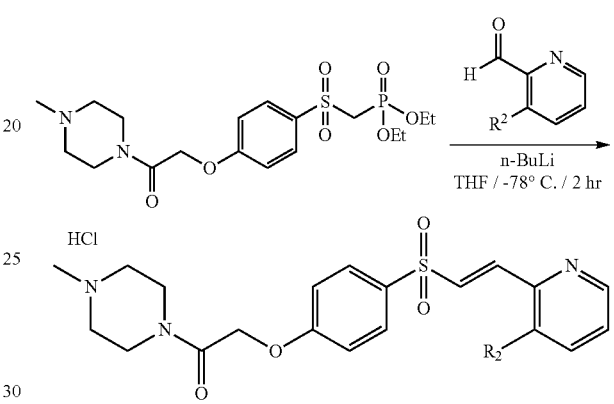

After dissolving diethyl (4-(2-(4-methylpiperazin-1-yl)-2-oxoethoxy)phenylsulfonyl)methylphosphonate (1 eq) prepared according to Preparation Examples 1 to 3 in anhydrous THF (0.1 M), the reaction mixture was cooled to −78° C. using dry ice and acetone. n-BuLi (1.2 eq, 2.0 M cyclohexane solution) was slowly added dropwise to the mixture and stirred for 1 hour, and then 3-fluoropicolinaldehyde (1.2 eq) was added and reacted again for another hour. If the reaction was not completed when confirmed by TLC, the reaction was carried out for another 30 minutes at room temperature. After the reaction was terminated with a small amount of water, the reaction mixture was extracted with water and 10% MeOH/MC, a small amount of water was removed from the organic layer using anhydrous $Na_2SO_4$, and the solvent was removed by distillation under reduced pressure and vacuum-dried. Thereafter, the products were separated and purified by column chromatography using EtOAc and 10% MeOH/MC to obtain (E)-2-(4-(2-(3-fluoropyridin-2-yl)vinylsulfonyl)phenoxy)-1-(4-methylpiperazin-1-yl)ethanone. After dissolving the thus-obtained compound in EtOAc, an excess of HCl (4.0 M 1,4-dioxane solution) was added dropwise, and the reaction mixture was reacted at room temperature for 2 hours. Subsequently, the thus-formed precipitates were filtered while washing several times with hexane and EtOAc, and separated and purified by column chromatography using EtOAc and 10% MeOH/MC to obtain (E)-2-(4-(2-(3-fluoropyridin-2-yl)vinylsulfonyl)phenoxy)-1-(4-methylpiperazin-1-yl)ethanone hydrochloride.

Yield: 60%;
$R_f$=0.50 (10% MeOH/MC);
$^1$H NMR (400 MHz, DMSO): δ 2.75-3.63 (m, 10H), 4.00 (d, J=13.4 Hz, 1H), 4.36 (d, J=13.1 Hz, 1H), 4.69 (s, 2H), 5.10 (dd, J=14.7 Hz, 33.6 Hz, 2H), 7.19 (d, J=8.6 Hz, 2H), 7.57-7.90 (m, 6H), 8.49 (d, J=3.7 Hz, 1H), 11.72 (s, 1H);

$^{13}$C NMR (100 MHz, DMSO): δ 42.4, 52.3 (d, J$_{C-F}$=15.6 Hz), 66.1, 668, 116.1, 125.2 (d, J$_{C-F}$=18.8 Hz), 128.2 (d, J$_{C-F}$=4.4 Hz), 130.3, 131.7, 132.1, 134.0 (d, J$_{C-F}$=4.0 Hz), 139.1 (d, J$_{C-F}$=11.0 Hz), 146.8 (d, J$_{C-F}$=4.8 Hz), 158.5 (d, J$_{C-F}$=261.4 Hz), 159.8, 162.8.

Example 18: Synthesis of (E)-2-(4-(2-(3-chloropyridin-2-yl)vinylsulfonyl)phenoxy)-1-(4-methylpiperazin-1-yl)ethanone hydrochloride (Compound 18)

The reaction was performed in the same manner as in Example 17 to obtain (E)-2-(4-(2-(3-chloropyridin-2-yl)vinylsulfonyl)phenoxy)-1-(4-methylpiperazin-1-yl)ethenone hydrochloride, except that 3-chloropicolinaldehyde was used instead of 3-fluoropicolinaldehyde.

Yield: 66%;
R$_f$=0.50 (10% MeOH/MC);
$^1$H NMR (400 MHz, DMSO): δ 2.76-3.11 (m, 6H), 3.99 (d, J=13.6 Hz, 1H), 4.37 (d, J=13.4 Hz, 1H), 5.09 (dd, J=14.5 Hz, 31.4 Hz, 2H), 7.18 (d, J=8.7 Hz, 2H), 7.51-7.54 (m, 1H), 7.72 (d, J=14.7 Hz, 1H), 7.85-7.91 (m, 3H), 8.06 (d, J=8.1 Hz, 1H), 859 (d, J=4.0 Hz, 1H), 11.28 (s, 1H);
$^{13}$C NMR (100 MHz, DMSO): δ 42.5, 52.5, 66.0, 99.1, 116.2, 127.4, 130.3, 131.6, 132.5, 134.4, 135.2, 138.8, 147.5, 149.0, 162.8, 165.9.

The types and positions of the substituents of Compounds 1 to 18 synthesized according to Examples 1 to 18 are shown in Table 4 below.

TABLE 4

| Category | R$_1$ | X | N |
|---|---|---|---|
| Compound1 | Ortho-F | 6-F | Ortho |
| Compound2 | Meta-F | 6-F | Ortho |
| Compound3 | Para-F | 6-F | Ortho |
| Compound4 | Ortho-F | 6-Cl | Ortho |
| Compound5 | Meta-F | 6-Cl | Ortho |
| Compound6 | Para-F | 6-Cl | Ortho |
| Compound7 | Ortho-Cl | 6-F | Ortho |
| Compound8 | Meta-Cl | 6-F | Ortho |
| Compound9 | Para-Cl | 6-F | Ortho |
| Compound10 | Ortho-Cl | 6-Cl | Ortho |
| Compound11 | Meta-Cl | 6-Cl | Ortho |
| Compound12 | Para-Cl | 6-Cl | Ortho |
| Compound13 | Ortho-Cl | 2-Cl | Ortho |
| Compound14 | Ortho-Cl | 1-Cl | Meta |
| Compound15 | Para- (morpholinopropoxy) | 6-F | Ortho |
| Compound16 | Meta- (morpholinopropoxy) | 6-F | Ortho |
| Compound17 | Para- (methylpiperazinyl acetyl) | 6-F | Ortho |
| Compound18 | Para- (methylpiperazinyl acetyl) | 6-Cl | Ortho |

Experimental Example 1: Effect of Inducing Nrf2 Activity

In order to confirm the pharmacological activity of the compounds synthesized according to Examples 1 to 18 of the present invention, the effects of the synthesized derivatives on inducing the activity of Nrf2, a major regulator of the defense against oxidative stress, were evaluated by constructing an Nrf2 functional cell-based assay (DiscoveRx). Specifically, U2OS cells were used, and after the cell pellet was released with CP 0 reagent, the cells were loaded in an amount of 80 μL into a 96-well plate at a density of 1.5×10$^4$ cells/well and incubated for 24 hours. The compounds synthesized according to Examples 1 to 18 were diluted 3 times in DMSO at 7 different concentrations to prepare a stock solution. 10 μL. of each compound solution was mixed with 90 μL of CP 0 and added in an amount of 20 μL to each well of the 96-well plate, and each experiment was repeated three times. As a positive control, the cells were treated with 5 μM of sulforaphane, and the plate was wrapped in foil and incubated for 6 hours. Substrate reagents 1 and 2 were added to the cell assay buffer and mixed, and then 50 μL of the substrate reagent was added to a 96-well plate per well, wrapped in foil, and incubated for 1 hour. Thereafter, the luminescence value was measured at all wavelengths and at integration time of 100 ms using a luminescence spectrophotometer (Molecular Devices). The effect of each compound was expressed as a concentration that activates by 50% relative to the maximum effect exhibited at high concentration. The results are shown in Table 5 below, and the efficacy of the compounds was compared as a percentage with respect to the sulforaphane-treated group. As another control group, a chalcone derivative, VSC2 ((F)-1-(2-((2-methoxyphenyl)sulfonyl)vinyl)-2-chlorobenzene, Woo et al., *J. Med. Chem.*, 2014, 57:1473-1487), which has a parent structure similar to that of the present invention, and which has been confirmed to induce activation of Nrf2 through the structural changes of Keap1, was used.

TABLE 5

| Compound | Nrf2 EC$_{50}$ (μM) |
|---|---|
| Compound 1 | 0.176 |
| Compound 2 | 0.474 |
| Compound 3 | 0.542 |
| Compound 4 | 0.030 |
| Compound 5 | 0.084 |
| Compound 6 | 0.231 |
| Compound 7 | 0.122 |
| Compound 8 | 0.198 |
| Compound 9 | 0.286 |
| Compound 10 | 0.026 |
| Compound 11 | 0.046 |
| Compound 12 | 0.065 |
| Compound 13 | 0.147 |
| Compound 14 | 0.384 |

TABLE 5-continued

| Compound | Nrf2 EC$_{50}$ (µM) |
|---|---|
| Compound 15 | 0.346 |
| Compound 16 | 0.908 |
| Compound 17 | 1.204 |
| Compound 18 | 0.327 |
| VSC2 | 0.530 |
| SFN (sulforaphane) | 0.414 |

As shown in Table 5, all of the compounds of Examples 1 to 18 (Compounds 1 to 18) of the present invention were found to induce Nrf2 activity, and in particular, Compounds 1, 4 to 15, and 18 exhibited a superior effect on Nrf2 activation compared to sulforaphane and VSC2, which are well-known Nrf2 activators. Specifically, it was confirmed that Compound 10, which exhibited the most excellent activity among the compounds of the present invention, exhibited an excellent effect 15 times or more greater than sulforaphane. In particular, sulforaphane is known to exhibit high toxicity at a concentration of 5 µM or more due to strong non-selective reactivity despite its high activity since it contains an isothiocyanate group (NCS). The results according to Experimental Examples of the present invention suggest that the compounds of the present invention, which were confirmed to induce Nrf2 activity without exhibiting cytotoxicity even at a concentration of 10 µM, can be used as Nrf2 activators in place of sulforaphane.

Meanwhile, in order to confirm the relationship between the position of the substituent and the effect of inducing Nrf2 activity in the synthesized compounds, Compounds 1 to 3, 4 to 6, 7 to 9, and 10 to 12, which have the same substituent but at different positions, were each compared. As a result, it was confirmed that regardless of the type of substituents, the compounds having both the phenyl ring and the pyridinyl ring at the ortho position, and Compounds 1, 4, 7, and 10 showed superior activity compared to the compounds having the same substituent at different positions.

Experimental Example 2: Evaluation of Inhibitory Ability of CYP Activity

In order to confirm the possible application of the compounds according to the embodiments of the present invention as drugs to be substantially administered to the body, their ability to inhibit the activity of CYP, which is involved in about 75% of drug metabolism, was confirmed. Specifically, inhibition of activity was evaluated for the five isoenzymes 1A2, 2C9, 2C19, 2D6, and 3A4, which have been reported to account for at least 90% of the total metabolism by CYP based on the representatively selected Compounds 1, 4, 13, and 15 to 18. Human liver microsomes (0.25 mg/mL), 0.1 M phosphate buffer (pH 7.4), substrate drug cocktails of the five drug metabolites (phenacetin 50 µM, diclofenac 10 µM, (S)-mephenytoin 100 µM, dextromethorphan 5 µM, and midasolam 2.5 µM), and Compounds 1, 4, 13, and 15 to 18 were each added at a concentration of 0 µM or 10 µM and pre-incubated for 5 minutes at 37° C., a solution of the NADPH regeneration system was added thereto, and the mixture was incubated at 37° C. for 15 minutes. Thereafter, the reaction was terminated by adding an acetonitrile solution containing an internal standard substrate (terfenadine), followed by centrifugation (14,000 rpm, 4° C.) for 5 minutes. Subsequently, the supernatant was injected into the LC-MS/MS system, and the metabolites of the substrate drugs were simultaneously analyzed to evaluate the inhibitory ability of these compounds on drug metabolic enzymes. The metabolites of each CYP isoenzyme indicator drug generated through the above reaction were analyzed using the Shimadzu Nexera XR system and TSQ vantage (Thermo). A Kinetex C18 column was used as the HPLC column, and distilled water containing 0.1% formic acid and acetonitrile containing 0.1% formic acid were used as the mobile phase. The generated metabolites were quantified using the quantification mode of multiple reaction monitoring (MRM), and data were analyzed with Xcalibur (version 1.6.1). The inhibitory ability of Examples 17 and 18, and VSC2 on the activity of each CYP isoenzyme was converted into % activity relative to the negative control, in which no compounds above were added, and the results are shown in Table 6 below.

TABLE 6

| Compound | 2C19 | 2D6 | 2C9 | 1A2 | 3A4 |
|---|---|---|---|---|---|
| Compound 1 | 65.9 | 87.0 | 100.0 | 96.0 | 100.0 |
| Compound 4 | 47.3 | 86.0 | 62.6 | 96.0 | 100.0 |
| Compound 13 | 40.0 | 100.0 | 100.0 | 94.0 | 86.0 |
| Compound 15 | 77.4 | 99.7 | 100.0 | 87.2 | 97.4 |
| Compound 16 | 63.1 | 96.0 | 100.0 | 98.1 | 80.7 |
| Compound 17 | 83.9 | 93.0 | 122.0 | 95.6 | 96.2 |
| Compound 18 | 71.9 | 89.9 | 73.4 | 93.9 | 91.1 |
| VSC2 | 16.8 | 54.9 | 100.0 | 37.9 | 55.6 |

As shown in Table 6, as a result of evaluating the possibility of the drug metabolic enzyme-drug interaction for each of the compounds, the compounds of the present invention improved the inhibitory activity against most of the CYP isoenzymes compared to VSC2. The compounds of the present invention did not show inhibitory activity against the five CYP isoenzymes, which indicates that there is little possibility of drug interaction compared to VSC2.

Experimental Example 3: Evaluation of Metabolic Stability

Metabolic stability is a factor that can affect pharmacokinetic parameters (PK parameters) such as drug clearance, half-life, and oral bioavailability, and accordingly, it is one of the properties that the group of drug candidates should possess. Thus, in order to predict the degree of drug metabolism by the liver, which is the major organ of drug metabolism, through an in vitro experiment, metabolic stability of drugs was evaluated using liver microsomes. Specifically, a stability test was conducted using microsomes, which confirms the amount of the remaining drug by treating the candidate drugs, Compounds 1, 4, 13, 15, and 17 among the compounds of the present invention, and VSC2 to microsomes and incubating for a certain period of time. Specifically, the compounds were added to human liver microsomes (0.5 mg/mL) and 0.1 M phosphate buffer (pH 6.4) at a concentration of 1 µM, and the mixture was pre-incubated for 5 minutes at 37° C., and then the solution of NADPH regeneration system was added thereto and incubated for 30 minutes at 37° C. Thereafter the reaction was terminated by adding an acetonitrile solution containing an internal standard substance (chlorpropamide), followed by centrifugation for 5 minutes (14,000 rpm, 4° C.), and then the supernatant was injected into the LC-MS/MS system to analyze the substrate drug, thereby evaluating the metabolic stability for these compounds. The amount of substrate remaining by the reaction was analyzed using the Shimadzu Nexera XR system and TSQ vantage. A Kinetex C18 column was used as the HPLC column, and distilled water containing 0.1% formic acid and acetonitrile containing 0.1% formic acid were used as the mobile phase. Data was analyzed with Xcalibur (version 1.6.1), and the results are shown in Table 7 below.

TABLE 7

| Compound | Percentage of compounds remaining without being degraded by metabolism after 30 minutes (%) |
| --- | --- |
| Compound 1 | 95 |
| Compound 4 | 86 |
| Compound 13 | 99 |
| Compound 15 | 94 |
| Compound 17 | 94 |
| VSC2 | 20 |

As shown in Table 7, as a result of measuring the amount of drug remaining after incubating each compound with microsomes for 30 minutes, it was confirmed that Compounds 1, 4, 13, 15, and 17 of the present invention all remained at 85% or more and up to 99%. These results indicate that all compounds according to Examples of the present invention have a significantly improved stability against human liver microsomes compared to the control group VSC2.

Experimental Example 4: Evaluation of Solubility

In the development of new drugs, the solubility of drugs is one of the very important factors associated with the bio-absorption rate. For example, compounds having low solubility in an aqueous solution may generally exhibit a low bio-absorption rate. In addition, drugs with low solubility may crystallize in tissues or cause serious toxicity, and thus, the FDA requires additional research results on oral drugs with low solubility. Furthermore, low solubility may also be the biggest cause of failure in the development of candidate materials. Accordingly, the solubility of Compounds 1 to 18 of the present invention in water was measured, and as a result, it was confirmed that Compounds 15 and 16, which are compounds containing a morpholinyl group as a substituent, exhibited high solubility. Specifically, Compound 15 exhibited a high solubility of 10 mg/mL or more. It was shown that Compound 15, in which a morpholinyl group was introduced, had a solubility significantly higher than that of the control group, that is, VSC2 (S 0.01 mg/mL), a synthetic compound known to induce activation of existing Nrf2. In addition, these results indicate that the solubility can be improved by introducing a morpholinyl group when designing a drug.

Experimental Example 5: Evaluation of hERG Channel-Binding Inhibitory Ability

The human ether-a-go-go-related gene (hERG) ion channel is an important component of cardiac repolarization, and inhibitors of this channel can induce arrhythmia and sudden death. Therefore, if a candidate substance is identified as a potential inhibitor of the hERG ion channel during the development of a new drug, it may cause side effects due to cardiac toxicity, and thus efforts to minimize such side effects are needed. When a fluorescent hERG channel tracer binds to a membrane containing the hERG channel protein, the rotation of the tracer is restricted, thereby maintaining a high polarization state. However, when a competitive inhibitor binds to the hERG channel, the tracer is competitively pushed away from the membrane and depolarized as it loses its direction. By using such principal, the hERG-binding inhibitory ability of the compounds of the present invention was confirmed. As the compound of the present invention, Compound 15, which exhibited an excellent pharmacological activity and high solubility in aqueous solutions, and which is thus expected to have a high bio-absorption rate, was selected as a representative compound. The positive control was prepared as follows: E-4031 compound was diluted three-fold stepwise and mixed with an hERG channel-containing membrane prepared in advance and a fluorescent tracer, and the mixture was reacted for 4 hours, and subsequently, the polarization value according to the concentration was measured to calculate the $IC_{50}$ value. In the case of Compound 15, fluorescence intensity was measured at various concentrations, and then the $IC_{50}$ value was calculated compared to the control group, and as a result, it was confirmed that Compound 15 had an $IC_{50}$ value of 20 µM. These results indicate that the compound of the present invention is a compound in which safety has been secured, since it exhibited cardiac toxicity at a high concentration of 20 µM or more.

Experimental Example 6: Effect on Nrf2 Activation In Vitro

Through Experimental Example 1, the activation of Nrf2 by the compounds of the present invention was indirectly confirmed. Thus, in order to directly confirm the effect of the compounds of the present invention on Nrf2 activation, Western blot was performed. Compound 15 was selected as a representative compound synthesized by the present invention, and it was treated at different concentrations, and the accumulation of Nrf2 in the nucleus and/or the degree thereof were confirmed. Specifically, BV2 cells were loaded in a 25T flask at a density of $2 \times 10^6$ cells/flask in an amount of 4 mL and incubated in RPM1640 medium for 24 hours. The next day, Compound 15 was prepared by mixing in each medium so that the final concentration was 0 µM to 10 µM under a 0.1% DMSO condition, and then cells were added thereto and incubated for 6 hours. The thus-incubated cells were recovered, and the nucleus and cytoplasmic extracts were separated. The thus-separated nuclear extract was electrophoresed by 10% SDS-PAGE, transferred to a PVDF membrane, and blocked with bovine serum albumin (BSA). Thereafter, the amount of Nrf2 protein in the nucleus was measured using an anti-Nrf2 antibody, and the results are shown in FIG. 1. The amount of Nrf2 was measured relative to Lamin B1, which refers to the same amount of nuclear extract.

As shown in FIG. 1, Nrf2 was hardly found in the nuclear extract (0 µM) of the cells not treated with Compound 15, but the amount of Nrf2 gradually increased from the cells treated with Compound 15 at a concentration of 0.1 µM, and a significant amount of Nrf2 was detected in the cells treated at a concentration of 10 µM. This indicates that the compound of the present invention promotes the activation of Nrf2 in a concentration-dependent manner.

Experimental Example 7: Effect on Expression of Nrf2-Related Antioxidant Protein In Vitro As a transcription factor, Nrf2 acts to protect cells by increasing antioxidant enzymes in the nucleus. Through preceding Experimental Examples 1 and 6, the activation of Nrf2 by the compound of the present invention was confirmed directly or indirectly. Thus, whether the activated Nrf2 increases antioxidant enzymes was confirmed by measuring the amount of antioxidant enzymes using Western blot. As antioxidant enzymes to be detected, GCLC, GCLM, and HO-1, expression of which is known to increase due to Nrf2, were selected. Specifically, BV2 cells were loaded at a density of $5\times10^5$ cells/well in a 6-well plate in an amount of 1.5 mL, and incubated in RPM1640 medium for 24 hours. The next day, Compound 15 was prepared by mixing in each medium so that the final concentration was 0 µM to 10 µM under a 0.1% DMSO condition, and then cells were added thereto and incubated for 24 hours. The thus-incubated cells were recovered and lysed to extract the total protein, and then subjected to electrophoresis by 10% SDS-PAGE. The total extract subjected to electrophoresis was transferred to a PVDF membrane and then blocked with bovine serum albumin. Thereafter, the amount of antioxidant enzymes expressed in cells was measured using antibodies corresponding to each antioxidant enzyme, and the results are shown in FIG. 2.

Figure 2:
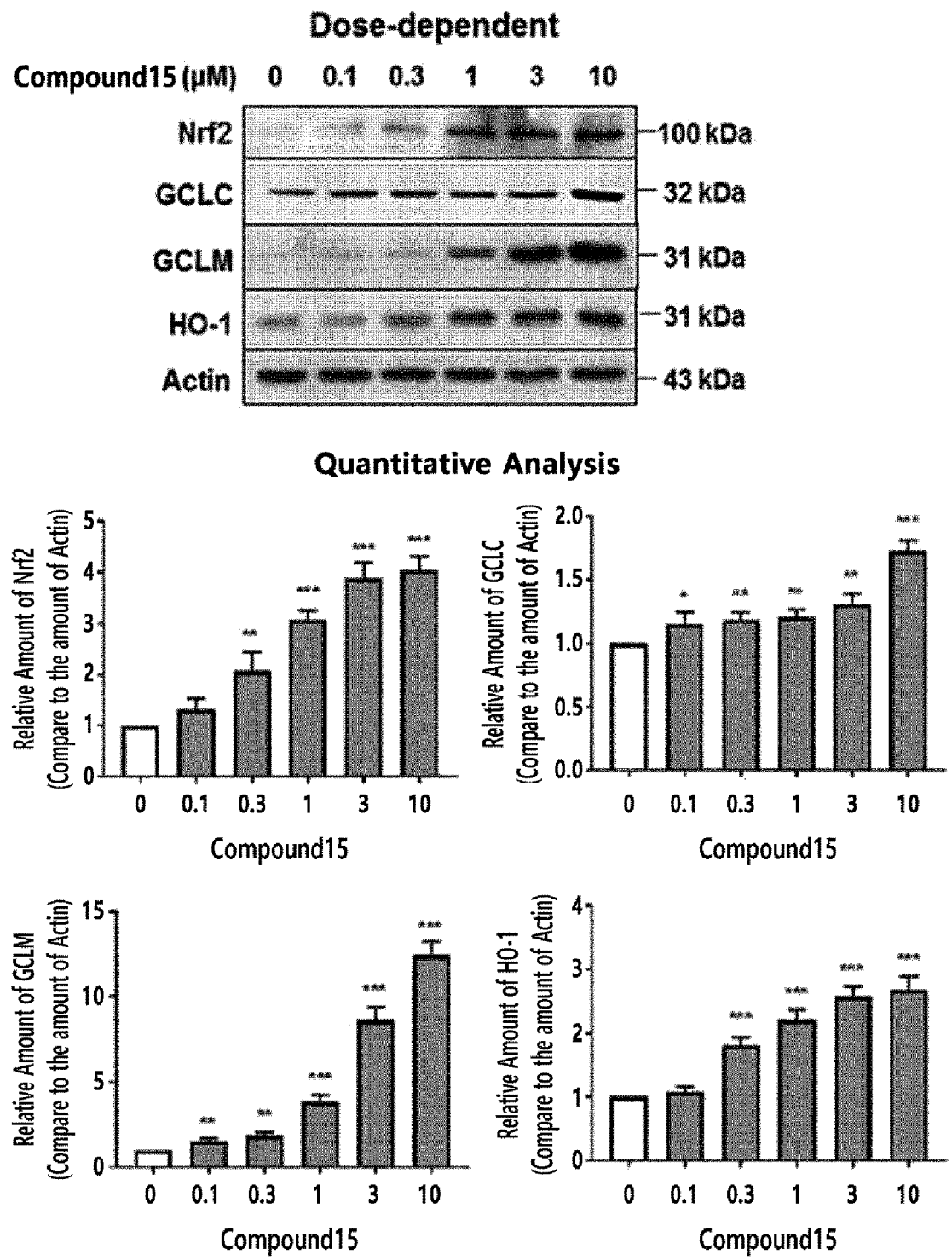
FIG. 2 is a diagram showing the result of quantitatively analyzing the Nrf2 activation and expression of a series of antioxidant enzymes, GCLC, GCLM, and HO-1, which are related thereto, according to the concentration of the compound according to one embodiment of the present invention.

As shown in FIG. 2, Nrf2 and antioxidant enzymes, namely GCLC, GCLM, and HO-1, were quantified relative to actin protein, which refers to the same amount of the total extract. The expression level tended to increase according to the concentration of Compound 15 treated, based on all of the enzymes tested. Specifically, when Compound 15 was not treated to cells or treated at a low concentration of 0.1 µM, the difference in expression of antioxidant enzymes was not remarkable enough to be identified with the naked eye, but after 1 µM, a remarkable increase in Nrf2 and antioxidant enzymes was visually confirmed, and all showed the highest expression at 10 µM. These results indicate that the compound of the present invention, for example, Compound 15, increased the expression of antioxidant enzymes through Nrf2 activation in a concentration-dependent manner, and thus can exhibit an effect of protecting cells.

Figure 3:
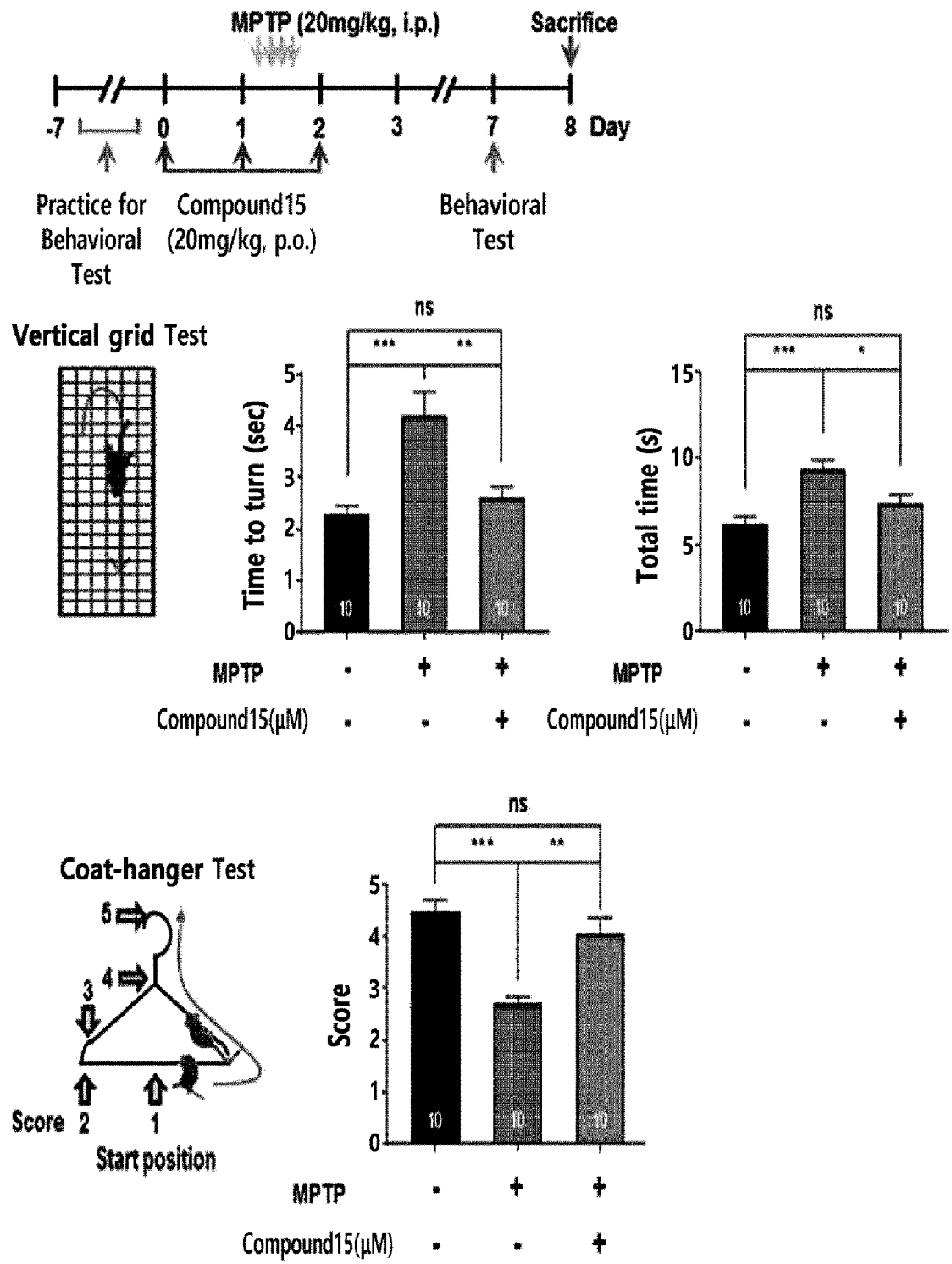
FIG. 3 is a diagram showing the MPTP-induced Parkinson's disease animal test model and effect on exercise capacity of the compound according to one embodiment of the present invention measured using the same.

Experimental Example 8: Cytoprotective Effect in Parkinson's Disease Model MPTP Mice In Experimental Examples 6 and 7, it was directly demonstrated that Compound 15 of the present invention activated Nrf2 in cells and increased the expression of antioxidant enzymes through in vitro experiments. Thus, in order to confirm whether the compounds of the present invention exhibit a cytoprotective effect even in an animal model, a mouse animal model was used in which Parkinson's disease was induced by killing only dopaminergic neurons by administering MPTP (1-methyl-4-phenyl-1,2,3,6-tetrahydropyridine), a neurotoxic substance. A specifically designed animal experiment schedule is shown at the top of FIG. 3. 10-week-old C57/BL6 mice were used as an animal model, and the animal model was prepared by dividing into three groups: a negative control group in which physiological saline was intraperitoneally injected, and in which a solution containing no Compound 15 was administered orally; a positive control group in which MPTP was intraperitoneally injected, and in which a solution containing no Compound 15 was administered orally; and an experimental group in which MPTP was intraperitoneally injected, and in which a solution containing Compound 15 was administered orally. The MPTP-induced Parkinson's disease model was prepared by injecting 20 mg/kg of MPTP intraperitoneally at 2-hour intervals a total of 4 times in a day. In the negative control group, physiological saline solution containing no MPTP was injected at the same time. In order to confirm whether or not Parkinson's disease was induced, motor impairment caused by dopaminergic neuronal cell death, known as the main symptom of Parkinson's disease, was confirmed by a vertical grid test and a coat-hanger test. Compound 15 was orally administered at a dose of 20 mg/mL once a day for 3 days from the day before MPTP injection, and behavioral experiments were conducted after 6 days from the day of MPTP injection, and the results are shown in the center and bottom of FIG. 3.

The vertical grid test evaluates the time to climb down when an experimental animal model is placed on a vertical ladder. In the present invention, the time to turn towards the floor and the total time taken to climb down from the ladder were measured once the mice were placed on a ladder. As shown in the graph in the center of FIG. 3, in the positive control group injected only with MPTP, both the time to turn and the total time were increased compared to the negative control group, which represented the normal mice, indicating that the exercise ability was decreased in the MPTP-induced Parkinson's disease model. On the other hand, in the case of the experimental group administered with Compound 15 of the present invention, both the time to turn and the total time were reduced again to a level similar to that of the negative control group, showing a significant difference from the positive control group described above.

The coat-hanger test, which is another behavioral experiment that evaluates exercise ability, was conducted as follows, as shown in the bottom left of FIG. 3: when the mice were placed in the middle of a hanger 30 cm away from the floor, the mice moved toward a safe position on the top of the hanger while being hanged, and a score was assigned according to the position at the time point with a time limit of 3 minutes. The specific experimental method and the result are shown at the bottom of FIG. 3. As shown in the graph at the bottom of FIG. 3, most of the negative control moved to the top of the hanger, corresponding to 5 points, but in the case of the positive control, 2 to 3 points were recorded because the mice mainly stopped at both ends of the bottom of the hanger. However, in the experimental group administered with Compound 15 of the present invention, a significant number of mice moved to the top, corresponding to 4 or 5 points, showing a high score of 4 points or more on average.

As a result of summarizing the two exercise ability tests above, it was confirmed that the compound of the present invention restored the exercise ability reduced by MPTP to a level similar to that of normal mice.

Experimental Example 9: Effect on Dopaminergic Neurons in Parkinson's Disease Model MPTP Mice From the results of Experimental Example 8, the effect of restoring exercise ability by the compound of the present invention was confirmed. In order to confirm whether the recovery of such exercise ability was due to the neuroprotective effect of the compounds of the present invention, brains were excised from mice and analyzed by immunohistochemical staining using tyrosine hydroxylase used as a marker for dopaminergic neurons. As a site for analysis, the corpus striatum and substantia nigra, which are concentrated with dopaminergic neurons, were selected.

Figure 4:
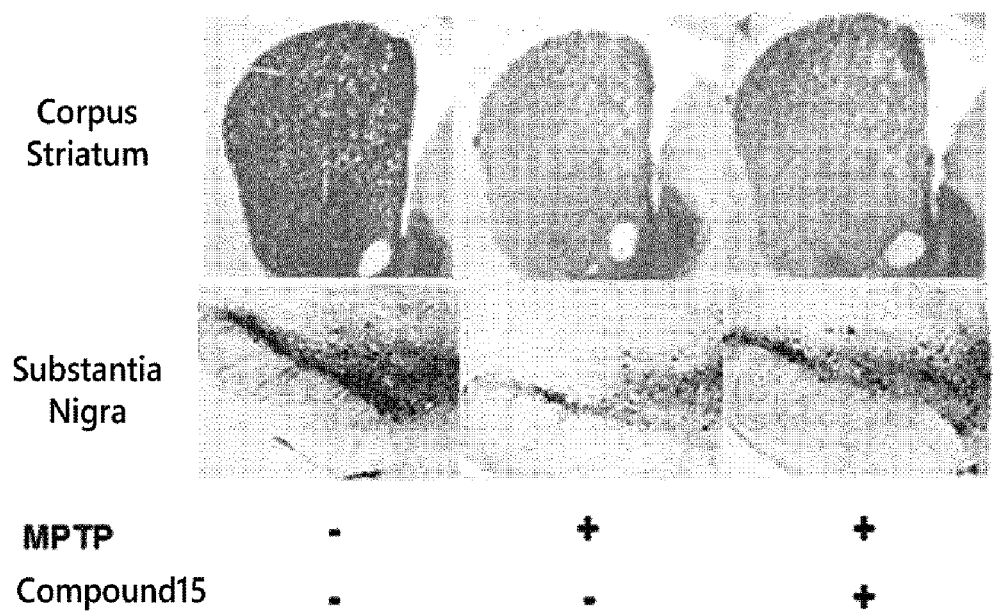
FIG. 4 is a diagram showing the effect of the compound according to one embodiment of the present invention on the protection of dopaminergic neurons in the MPTP-induced Parkinson's disease animal test model.

Specifically, after anesthetizing the mice in the negative control group, the positive control group, and the experimental group with avertin, physiological saline and 4% formaldehyde were injected into the heart, and the brain was excised, which was sequentially immersed in 4% formaldehyde and 30% sucrose, and stored in the refrigerator for one day each. Thereafter, the tissue fragments of the corpus striatum and substantia nigra were obtained from the stored brain using a cryosectioning machine. The brain tissue fragments were stained by DAB staining using a tyrosine hydroxylase antibody, which is specifically expressed in dopaminergic neurons, by immunohistochemical staining, and observed with a microscope, and the results are shown in FIG. 4. The regions containing tyrosine hydroxylase were stained brown by the immunohistochemical staining, indicating that live dopaminergic neurons were present. As shown on the left side of FIG. 4, the stained corpus striatum and substantia nigra of the negative control group, which represented the normal mice, showed a dark brown color, but the staining was considerably lighter in the positive control group in which the disease was induced by MPTP. This may be due to the death of many dopaminergic neurons by MPTP treatment. On the other hand, in the experimental group treated with Compound 15 of the present invention, the staining became dark again, which is believed to be due to the cytoprotective effect which inhibited the death of dopaminergic neurons caused by MPTP based on the antioxidant effect according to the administration of Compound 15. Accordingly, the results show that the compound of the present invention has the effect of preventing or treating neurodegenerative diseases such as Parkinson's disease caused by dopaminergic neuronal death.

Comparative Examples 1 and 2: Comparison of Activity with Known Chalcone Compounds As drug candidates, in order to demonstrate the effect of the compounds of the present invention, two compounds having excellent activity among known chalcone derivatives known to induce Nrf2 activation, namely, (E)-1-chloro-2-(2-(2-methoxyphenylsulfonyl)vinyl)benzene (VSC2, Comparative Example 1) and (E)-2-chloro-3-(2-(2-methoxyphenylsulfonyl)vinyl)pyridine (Comparative Example 2) were synthesized and used as Comparative examples. These compounds are disclosed in Korean Patent No. 10-1438655 and *J. Med. Chem.*, 2014, 57:1473-1487. In order to confirm the utility as a real drug, in addition to the effect of inducing Nrf2 activity, solubility involved with bioavailability, metabolic stability, and hERG channel-binding inhibitory ability involved with cardiotoxicity were also confirmed, and the results are shown in Table 8 below, As shown in Table 8, although the compounds of Comparative Examples 1 and 2 had an effect of inducing Nrf2 activity, the effect was about 60% and 10% of the level of Compound 15. In addition, Compound 15 did not show an inhibitory activity against 5 types of CYP isoenzymes, but the compounds of Comparative Examples 1 and 2 showed a remarkable inhibitory activity against some CYP isoenzymes. Further, the residual amounts of the compounds of Comparative Examples 1 and 2 were reduced to 20% and 62%, respectively, by 30-minute incubation with human liver microsomes, whereas the residual amount of Compound 15 was maintained at 94% under the same conditions, thereby confirming that Compound 15 had a significantly higher metabolic stability compared to the compounds of the Comparative Examples. Meanwhile, both of the compounds of Comparative Examples 1 and 2 had a low solubility of less than 0.01 mg/mL, and thus were expected to have remarkably low bioavailability, whereas Compound 15 had a high solubility of more than 10 mg/mL due to the introduction of a morpholinyl group, and was expected to exhibit high bioavailability. Finally, as a result of confirming the hERG channel-binding inhibitory ability involved with cardiac toxicity, it was confirmed that the compounds of Comparative Examples 1 and 2 exhibited a low $IC_{50}$ value of 1 μM, showing that there is a possibility of cardiac toxicity when administered to the body. However, Compound 15 exhibited a high $IC_{50}$ value of 20 μM, indicating that it is a safe compound that does not exhibit cardiac toxicity even when administered in an effective amount for conventional treatment.

The invention claimed is:
1. A compound represented by Chemical Formula 1 below or a pharmaceutically acceptable salt thereof:

[Chemical Formula 1]

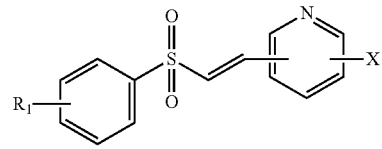

TABLE 8

|  | Comparative Example 1 | | | | | Comparative Example 2 | | | | | Compound 15 | | | | |
| --- | --- | --- | --- | --- | --- | --- | --- | --- | --- | --- | --- | --- | --- | --- | --- |
| Effect of Inducing Nrf2 Activity ($EC_{50}$) | 0.530 μM | | | | | 3.23 μM | | | | | 0.327 μM | | | | |
| Inhibitory Ability of CYP Activity (%) | 2C19 | 2D6 | 2C9 | 1A2 | 3A4 | 2C19 | 2D6 | 2C9 | 1A2 | 3A4 | 2C19 | 2D6 | 2C9 | 1A2 | 3A4 |
|  | 16.8 | 54.9 | 100 | 37.0 | 55.6 | 62.7 | 48.0 | 100 | 60.5 | 34.1 | 77.4 | 88.6 | 100 | 82.6 | 85.8 |
| Metabolic Stability in Human Liver (Amount of Residual Compound, %) | | | 20 | | | | | 62 | | | | | 94 | | |
| Solubility of Drug (mg/mL) | <0.01 | | | | | <0.01 | | | | | >10 | | | | |
| hERG Channel-Binding Inhibition ($IC_{50}$) | 1.2 μM | | | | | 1.14 μM | | | | | 20 μM | | | | | wherein, in the Chemical Formula 1,

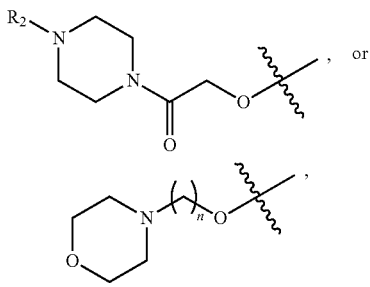

$R_1$ is a halogen,
$R_2$ is hydrogen or $C_{1-4}$ alkyl,
n is an integer of 1 to 5, and
X is a halogen.

2. The compound or a pharmaceutically acceptable salt thereof of claim 1, wherein $R_1$ is chlorine or fluorine, and X is chlorine or fluorine.

3. The compound or a pharmaceutically acceptable salt thereof of claim 1, wherein $R_1$ is

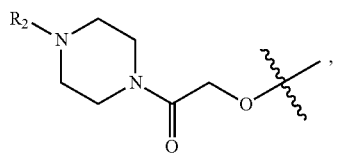

$R_2$ is methyl, and X is chlorine or fluorine.

4. The compound or a pharmaceutically acceptable salt thereof of claim 1, wherein $R_1$ is

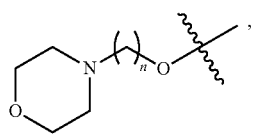

n is 3, and X is chlorine or fluorine.

5. The compound or a pharmaceutically acceptable salt thereof of claim 1, wherein the compound is
1. (E)-3-fluoro-2-(2-(2-fluorophenylsulfonyl)vinyl)pyridine,
2. (E)-3-fluoro-2-(2-(3-fluorophenylsulfonyl)vinyl)pyridine,
3. (E)-3-fluoro-2-(2-(4-fluorophenylsulfonyl)vinyl)pyridine,
4. (E)-3-chloro-2-(2-(2-fluorophenylsulfonyl)vinyl)pyridine,
5. (E)-3-chloro-2-(2-(3-fluorophenylsulfonyl)vinyl)pyridine,
6. (E)-3-chloro-2-(2-(4-fluorophenylsulfonyl)vinyl)pyridine,
7. (E)-2-(2-(2-chlorophenylsulfonyl)vinyl)-3-fluoropyridine,
8. (E)-2-(2-(3-chlorophenylsulfonyl)vinyl)-3-fluoropyridine,
9. (E)-2-(2-(4-chlorophenylsulfonyl)vinyl)-3-fluoropyridine,
10. (E)-3-chloro-2-(2-(2-chlorophenylsulfonyl)vinyl)pyridine,
11. (E)-3-chloro-2-(2-(3-chlorophenylsulfonyl)vinyl)pyridine,
12. (E)-3-chloro-2-(2-(4-chlorophenylsulfonyl)vinyl)pyridine,
13. (E)-2-chloro-6-(2-(2-chlorophenylsulfonyl)vinyl)pyrimidine,
14. (E)-2-chloro-3-(2-(2-chlorophenylsulfonyl)vinyl)pyrimidine,
15. (E)-4-(3-(4-(2-(3-fluoropyridin-2-yl)vinylsulfonyl)phenoxy)propyl)morpholine,
16. (E)-4-(3-(3-(2-(3-fluoropyridin-2-yl)vinylsulfonyl)phenoxy)propyl)morpholine,
17. (E)-2-(4-(2-(3-fluoropyridin-2-yl)vinylsulfonyl)phenoxy)-1-(4-methylpiperazin-1-yl)ethanone, or
18. (E)-2-(4-(2-(3-chloropyridin-2-yl)vinylsulfonyl)phenoxy)-1-(4-methylpiperazin-1-yl)ethanone.

6. A nuclear factor erythroid-derived 2-related factor 2 (Nrf2) activator comprising the compound of claim 1 or a pharmaceutically acceptable salt thereof as an active ingredient.

7. A pharmaceutical composition for preventing or treating diseases induced by a decrease in Nrf2 activity, comprising the compound of claim 1 or a pharmaceutically acceptable salt thereof as an active ingredient.

8. The pharmaceutical composition of claim 7, wherein the diseases induced by a decrease in Nrf2 activity are liver diseases selected from the group consisting of alcoholic liver disease, non-alcoholic liver disease, non-alcoholic fatty liver disease (NAFLD), chronic liver injury, viral hepatitis, and hepatocellular carcinoma; kidney diseases selected from the group consisting of diabetic nephropathy, focal segmental glomerulosclerosis, renal fibrosis, lupus-like autoimmune nephritis, chronic kidney disease (CKD), and hypertensive kidney disease; pulmonary diseases selected from the group consisting of chronic obstructive pulmonary disease (COPD), pulmonary emphysema, ventilation-associated lung injury, acute lung injury (ALI), acute respiratory distress syndrome (ARDS), pulmonary artery hypertension (PAH), and right heart failure induced by pulmonary artery hypertension; neurodegenerative diseases selected from the group consisting of Parkinson's disease (PD), Alzheimer's disease (AD), Huntington's disease, Lou Gehrig's disease, epilepsy, depression, insomnia, anxiety, and multiple sclerosis (MS); mitochondrial myopathy; Friedreich's ataxia; corneal endothelial cell loss; or psoriasis.

9. A method for producing the compound of claim 1 or a pharmaceutically acceptable salt thereof, comprising reacting diethyl (($R_1$-substituted phenyl)sulfonyl)methylphosphonate with halopicolinealdehyde, wherein $R_1$ is a halogen,

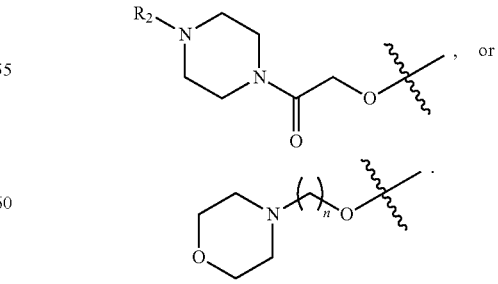

10. The method of claim 9, wherein the reaction is carried out by cooling the mixture of diethyl (($R_1$-substituted phenyl)sulfonyl)methylphosphonate and halopicolinealdehyde to −100° C. to −60° C. under anhydrous organic solvent conditions, and then adding butyllithium.

11. The method of claim 9 further comprising allowing to react with an excess acidic solution after the reaction.

12. The method of claim 9, wherein when $R_1$ is

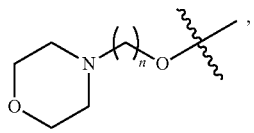

diethyl ((R$_1$-substituted phenyl)sulfonyl)methylphosphonate is prepared through:
Step a-1 of reacting (hydroxy-C$_{1-5}$ alkyl)morpholine with methanesulfonyl halide to prepare morpholino(C$_{1-5}$ alkyl) methanesulfonate; and
Step a-2 of reacting morpholino(C$_{1-5}$ alkyl) methanesulfonate with diethyl (hydroxyphenylsulfonyl)methylphosphonate.

13. The method of claim 12, wherein the Step a-1 is carried out by adding methanesulfonyl halide and a base to a solution in which (hydroxy-C$_{1-5}$ alkyl)morpholine is dissolved in an organic solvent at −10° C. to 10° C., and then reacting at 10° C. to 35° C.

14. The method of claim 12, wherein the Step a-2 is carried out by mixing the reactants at 10° C. to 35° C. and heating to 70° C. to 90° C. in the presence of 1 to 2 equivalents of K$_2$CO$_3$ based on the amount of diethyl (hydroxyphenylsulfonyl)methylphosphonate used.

15. The method of claim 9, wherein when $R_1$ is

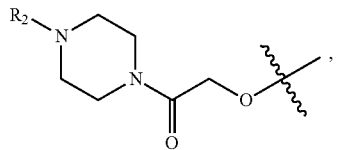

diethyl ((R$_1$-substituted phenyl)sulfonyl)methylphosphonate is prepared through:
Step b-1 of reacting diethyl (hydroxyphenylsulfonyl)methylphosphonate with C$_{1-4}$ alkyl haloacetate to prepare C$_{1-4}$ alkyl (((diethoxyphosphoryl)methylsulfonyl)phenoxy)acetate;
Step b-2 of converting ethyl (((diethoxyphosphoryl)methylsulfonyl)phenoxy)acetate to (((diethoxyphosphoryl)methylsulfonyl)phenoxy)acetic acid by sequentially treating with a basic solution and an acidic solution; and
Step b-3 of reacting (((diethoxyphosphoryl)methylsulfonyl)phenoxy)acetic acid with piperazine or 1-(C$_{1-4}$ alkyl)piperazine in the presence of 2 to 4 equivalents of carbonyldiimidazole to prepare diethyl ((2-(4-piperazin-1-yl)-2-oxoethoxy)phenylsulfonyl)methylphosphonate or diethyl ((2-(4-(C$_{1-4}$ alkyl)piperazin-1-yl)-2-oxoethoxy)phenylsulfonyl)methylphosphonate.

16. The method of claim 15, wherein the Step b-1 is carried by heating the mixture to 80° C. to 100° C. in the presence of 1 to 2 equivalents of K$_2$CO$_3$ based on the amount of diethyl (hydroxyphenylsulfonyl)methylphosphonate used.

17. The method of claim 15, wherein the Step b-2 is carried out at 10° C. to 40° C.

18. The method of claim 15, wherein the Step b-3 is carried out by reacting the reactant with carbonyldiimidazole at 10° C. to 40° C., and then adding piperazine or 1-(C$_{1-4}$ alkyl)piperazine, thereby allowing to react at 10° C. to 40° C.

19. The method of claim 12, wherein the diethyl (hydroxyphenylsulfonyl)methylphosphonate is prepared through:
Step c-1 of reacting diethyl hydroxymethylphosphonate with toluenesulfonyl halide to prepare (diethoxyphosphoryl)methyl methyl benzenesulfonate;
Step c-2 of reacting (diethoxyphosphoryl)methyl methyl benzenesulfonate with mercaptophenol to prepare (hydroxyphenylthio)methylphosphonate; and
Step c-3 of adding meta-chloroperoxybenzoic acid (mCPBA) to (hydroxyphenylthio)methylphosphonate at 0° C., and then allowing to react while stirring at room temperature.

20. The method of claim 15, wherein the diethyl (hydroxyphenylsulfonyl)methylphosphonate is prepared through:
Step c-1 of reacting diethyl hydroxymethylphosphonate with toluenesulfonyl halide to prepare (diethoxyphosphoryl)methyl methyl benzenesulfonate;
Step c-2 of reacting (diethoxyphosphoryl)methyl methyl benzenesulfonate with mercaptophenol to prepare (hydroxyphenylthio)methylphosphonate; and
Step c-3 of adding meta-chloroperoxybenzoic acid (mCPBA) to (hydroxyphenylthio)methylphosphonate at 0° C., and then allowing to react while stirring at room temperature.

* * * * *